United States Patent
Bitenc et al.

(10) Patent No.: US 10,823,744 B2
(45) Date of Patent: Nov. 3, 2020

(54) METHODS AND SYSTEMS FOR METABOLITE AND/OR LIPID-BASED DETECTION OF COLORECTAL CANCER AND/OR ADENOMATOUS POLYPS

(71) Applicant: Universal Diagnostics, S.L., Seville (ES)

(72) Inventors: Marko Bitenc, Seville (ES); Kristi Kruusmaa, Seville (ES); Paola Hurtado Castillo, Seville (ES); Ana María Jiménez Girón, Seville (ES); Rosa Argamasilla Martinez, Seville (ES); Andreu Fabregat Rossell, Seville (ES); Antonio Jesus Adsuar Gomez, Seville (ES); Juan Martinez-Barea, Seville (ES); Christian Hense, Seville (ES); Patricia Rodríguez Gómez, Seville (ES); Ángela Peralbo Molina, Seville (ES); Jorge Casado Agrelo, Seville (ES); Alejandro Sánchez Brotons, Seville (ES); Cristina Pavón Solís, Seville (ES); Rosa María Delgado Sánchez, Seville (ES)

(73) Assignee: Universal Diagnostics, S.L., Seville (ES)

( * ) Notice: Subject to any disclaimer, the term of this patent is extended or adjusted under 35 U.S.C. 154(b) by 165 days.

(21) Appl. No.: 15/725,158

(22) Filed: Oct. 4, 2017

(65) Prior Publication Data

US 2018/0196074 A1    Jul. 12, 2018

Related U.S. Application Data

(63) Continuation of application No. 15/458,568, filed on Mar. 14, 2017, now Pat. No. 10,006,925.

(Continued)

(51) Int. Cl.
*G01N 33/92* (2006.01)
*G01N 33/574* (2006.01)
(Continued)

(52) U.S. Cl.
CPC ....... *G01N 33/92* (2013.01); *G01N 33/57419* (2013.01); *G01N 33/57484* (2013.01);
(Continued)

(58) Field of Classification Search
None
See application file for complete search history.

(56) References Cited

U.S. PATENT DOCUMENTS

| 7,349,809 B2 | 3/2008 | Goodenowe |
|---|---|---|
| 7,865,312 B2 | 1/2011 | Goodenowe |

(Continued)

FOREIGN PATENT DOCUMENTS

| WO | WO-2001/057518 A2 | 8/2001 |
|---|---|---|
| WO | WO-2003/081506 A2 | 10/2003 |

(Continued)

OTHER PUBLICATIONS

Almendingen, K. et al., Familial adenomatous polyposis patients have high levels of arachidonic acid and docosahexaenoic acid and low levels of linoleic acid and [alpha]-linolenic acid in serum phospholipids, International Journal of Cancer, 120(3):632-637 (2006).

(Continued)

*Primary Examiner* — Xiaoyun R Xu
(74) *Attorney, Agent, or Firm* — William R. Haulbrook; Samuel R. Polio; Choate, Hall & Stewart LLP

(57) ABSTRACT

Described herein are sets of metabolite and lipid (e.g., fatty acid) markers that can be used in the detection of early stage colorectal cancer and/or early development of adenomatous polyps. Presented herein are illustrative pathology-linked (Continued)

panels. In certain embodiments, the markers presented herein (or subsets thereof) are used as a panel for detecting either colorectal cancer or adenomatous polyps at the same time. The markers presented herein include metabolites and lipids (e.g., fatty acid) freely detectable and accurately quantifiable in human serum. In certain embodiments, the sample may be plasma, urine, saliva, whole blood, dried blood spot or dried serum spot.

13 Claims, 8 Drawing Sheets
(1 of 8 Drawing Sheet(s) Filed in Color)

Related U.S. Application Data

(60) Provisional application No. 62/343,095, filed on May 30, 2016.

(51) Int. Cl.
    *G16H 50/20*     (2018.01)
    *G06F 19/00*     (2018.01)

(52) U.S. Cl.
    CPC ....... *G01N 33/57488* (2013.01); *G06F 19/00* (2013.01); *G16H 50/20* (2018.01); *G01N 2405/00* (2013.01); *G01N 2458/15* (2013.01); *G01N 2560/00* (2013.01); *G01N 2570/00* (2013.01); *G01N 2800/065* (2013.01); *G01N 2800/56* (2013.01)

(56) References Cited

U.S. PATENT DOCUMENTS

| | | |
|---|---|---|
| 8,409,794 B2 | 4/2013 | Ritchie et al. |
| 10,006,925 B2 | 6/2018 | Bitenc et al. |
| 2004/0044050 A1 | 3/2004 | Goodman et al. |
| 2006/0080042 A1 | 4/2006 | Goodenowe |
| 2008/0255764 A1 | 10/2008 | Ritchie et al. |
| 2010/0086960 A1 | 4/2010 | Ritchie et al. |
| 2012/0136057 A1 | 5/2012 | Ritchie et al. |
| 2012/0202188 A1 | 8/2012 | Pastural et al. |
| 2013/0110408 A1 | 5/2013 | Cook et al. |
| 2013/0330746 A1 | 12/2013 | Ritchie et al. |
| 2017/0343567 A1 | 11/2017 | Bitenc et al. |

FOREIGN PATENT DOCUMENTS

| | | |
|---|---|---|
| WO | WO-2007/030928 A2 | 3/2007 |
| WO | WO-2007/109881 A1 | 10/2007 |
| WO | WO-2008/092280 A1 | 8/2008 |
| WO | WO-2011/011882 A1 | 2/2011 |
| WO | WO-2011/038509 A1 | 4/2011 |
| WO | WO-2011/143779 A1 | 11/2011 |
| WO | WO-2011/143779 A1 | 11/2011 |
| WO | WO-2014/116833 A2 | 7/2014 |
| WO | WO-2015/109263 A2 | 7/2015 |
| WO | WO-2017/114955 A2 | 7/2017 |

OTHER PUBLICATIONS

Deng, L. et al., Combining NMR and LC/MS Using Backward Variable Elimination: Metabolomics Analysis of Colorectal Cancer, Polyps, and Healthy Controls, Analytical Chemistry, 88(16):7975-7983 (2016).

International Search Report, PCT/EP2017/063058, dated Nov. 27, 2017, 10 pages.

Jing, Y. et al., Rapid differentiating colorectal cancer and colorectal polyp using dried blood spot mass spectrometry metabolomic approach: Differentiating Colorectal Cancer and Colorectal Polyp, IUBMB Life, 69(5):374-354 (2017).

Kuwata, G. et al., Increase of $N^1,N^{12}$-diacetylspermine in tissues from colorectal cancer and its liver metastasis, J. Cancer Res. Clin. Oncol., 139:925-932 (2013).

Nakayama, Y., The clinical usefulness of urinary N1, N12-diacetylspermine CiAcSpm) levels as a tumor marker in patients with colorectal cancer, Oncology Letters, 2:970-974 (2012).

Tian, Y. et al., Tissue Metabonomic Phenotyping for Diagnosis and Prognosis of Human Colorectal Cancer, Scientific Reports, 6:20790 (2016).

Written Opinion, PCT/EP2017/063058, dated Nov. 27, 2017, 10 pages.

Yue, H. et al., A metabonomics study of colorectal cancer by RRLC-QTOF/MS, Journal of Liquid Chromatography & Related Technologies, 36(4):428-438 (2012).

Zhu, J. et al., Colorectal Cancer Detection Using Targeted Serum Metabolic Profiling, Journal of Proteome Research, 13(9):4120-4130 (2014).

International Search Report, PCT/EP2017/063058 (Methods and Systems for Metabolite and/or Lipid-Based Detection of Colorectal Cancer and/or Adenomatous Polyps, filed May 30, 2017), issued by ISA/EPO, dated Nov. 27, 2017, 10 pages.

Written Opinion, PCT/EP2017/063058 (Methods and Systems for Metabolite and/or Lipid-Based Detection of Colorectal Cancer and/or Adenomatous Polyps, filed May 30, 2017), issued by ISA/EPO, dated Nov. 27, 2017, 10 pages.

Arab, A. et al., The effects of conjugated linoleic acids on breast cancer: A systematic review, Advanced Biomedical Research, 6;5:115 (2016).

Bae, S. et al., Plasma Choline Metabolites and Colorectal Cancer Risk in the Women's Health Initiative Observational Study, Cancer Research, 74(24):7442-52 (2014).

Dai, J. R. et al., Triangulynes A-Hand Triangulynic Acid. New Cytotoxic Polyacetylenes from the Marine Sponge *Pellina triangulate*, J. Nat. Prod., 59:860-865 (1996).

De Marco, D. et al., Production of S-Sulfo-Cysteine and S-Sulfo-Cysteamine from Cystine and Cystamine, Coupled to Enzymic Transamination and Deamination of Cysteinesulfinic Acid, Biochimica et Biophysica Acta, 47:262-6 (1961).

Giskeødegård, G. F. et al., Metabolic markers in blood can separate prostate cancer from benign prostatic hyperplasia, British Journal of Cancer, 113(12):1712-17199 (2015).

Hall, M. N. et al. Blood Levels of Long-Chain Polyunsaturated Fatty Acids, Aspirin, and the Risk of Colorectal Cancer, Cancer Epidemiology, Biomarkers & Prevention, 16(2):314-321 (2007).

Jooste, S. et al., The detection of 3-methylglutarylcarnitine and a new dicarboxylic conjugate, 3-methylglutaconylcarnitine, in 3-methylglutaconic aciduria, Clinica Chimica Acta, 230(1):1-8 (1994).

Kato, M. et al., Prognostic Significance of Urine N1, N12-Diacetylspermine in Patients with Non-Small Cell Lung Cancer, Anticancer Research, 34(6):3053-3060 (2014).

Lie Ken Jie, M. S. F. and Cheung, Y. K., Synthesis and Nuclear Magnetic Resonance Studies on a Series of Synthetic Long-chain Selenophene Fatty Esters, J. Chem. Res. Synop., p. 392 (1993).

Montrose, D. C. et al., Metabolic Profiling, a Noninvasive Approach for the Detection of Experimental Colorectal Neoplasia, Cancer Prevention Research, 5(12):1358-1367 (2012).

Nishimura, S. et al., Corticatic Acids D end E. Polyacetylenic Geranylgeranyltransferase Type I Inhibitors from the Marine Sponge *Petrosia corticata*, J. Nat. Prod., 65:1353-1356 (2002).

Ortiz De Montellano, P.R. et al., Specific Inactivation of Hepatic Fatty Acid Hydroxylases by Acetylenic Fatty Acids, J. Biol. Chem., 259(7):4136-4141 (1984).

Partial International Search Report, PCT/EP2017/063058, (Methods and Systems for Metabolite and/or Lipid-Based Detection of Colorectal Cancer and/or Adenomatous Polyps, filed May 30, 2017), issued by ISA/EP dated Aug. 25, 2017, 2 pages.

Provisional Opinion Accompanying the Partial Search Result, PCT/EP2017/063058, (Methods and Systems for Metabolite and/or Lipid-Based Detection of Colorectal Cancer and/or Adenomatous Polyps, filed May 30, 2017), issued by ISA/EP dated Aug. 25, 2017, 7 pages.

(56) References Cited

OTHER PUBLICATIONS

Rashed, M.S. et al., Determination of urinary S-sulphocysteine, xanthine and hypoxanthine by liquid chromatography-electrospray tandem mass spectrometry, Biomedical Chromatography, 19(3):223-30 (2005).

Ritchie, S.A. et al., Reduced levels of hydroxylated, polyunsaturated ultra long-chain fatty acids in the serum of colorectal cancer patients: implications for early screening and detection, BMC Medicine, 8:13:1-20 (2010).

Roe, C. R., et al., Identification of 3-Methylglutarylcarnitine A New Diagnostic Metabolite of 3-Hydroxy-3-methylglutaryl-Coenzyme A Lyase Deficiency, J Clin Invest, 7(4):1391-4 (1986).

Sgoutas, D. S. et al., Chemical Synthesis of Tritium-labeled Linoleic Acid, Biochemistry, 3(3):406-411 (1964).

Umemori, Y. et al., Evaluating the utility of $N^1,N^{12}$-diacetylspermine and $N^1,N^8$-diacetylspermidine in urine as tumor markers for breast and colorectal cancers, Clinica Chimica Acta, 411(23-24):1894-1899 (2010).

Wikoff, W. R. et al., Metabolomics analysis reveals large effects of gut microflora on mammalian blood metabolites, PNAS, 106(10):3698-703 (2009).

Williams, H.R. et al., Differences in gut microbial metabolism are responsible for reduced hippurate synthesis in Crohn's disease, BMC Gastroenterology, 10:108:1-8 (2010).

Zhang, Y. et al., Serum Unsaturated Free Fatty Acids: A Potential Biomarker Panel for Early-Stage Detection of Colorectal Cancer, Journal of Cancer, 7(4):477-483 (2016).

Zock, P. L. and Katan, M. B., Linoleic acid intake and cancer risk: a review and meta-analysis, Am J Clin Nutr, 68(1):142-53 (1998).

3Me-glutaryl carnitine (S192)

L-cysteine S-sulfate (S153)

α-linolenic acid (S69)

METHODS AND SYSTEMS FOR METABOLITE AND/OR LIPID-BASED DETECTION OF COLORECTAL CANCER AND/OR ADENOMATOUS POLYPS

CROSS REFERENCE TO RELATED APPLICATION

This application is a continuation of U.S. patent application Ser. No. 15/458,568, filed on Mar. 14, 2017, which claims the benefit of U.S. Provisional Application No. 62/343,095, filed on May 30, 2016, the content of which is hereby incorporated by reference herein in its entirety.

FIELD OF THE INVENTION

This invention relates generally to methods and systems for measuring metabolites and lipids (e.g., fatty acids) in biological samples. In particular embodiments, the invention relates to methods and systems for detection of metabolites and lipids (e.g., fatty acids) in human serum or another biological sample to identify early stage colorectal cancer and/or early development of adenomatous polyps, for example, though not necessarily, at the same time.

BACKGROUND

Digestive malignant neoplasms including esophageal, gastric, and colorectal cancer are the most common cause of cancer induced death in the world. For example, colorectal cancer (CRC) is the third most common cancer in men (746,000 cases, 10.0% of total cancer cases) and the second most common cancer in women (614,000 cases, 9.2%) worldwide and it is the third most frequent cause of cancer mortality in the world for both genders. The European Union alone recorded 345,000 colorectal cancer incidences and 152,000 deaths from colorectal cancer in 2012.

To decrease mortality rates, various platforms for early stage cancer detection have been developed and tested to complete diagnostic evaluations on recruited eligible populations. However, it is difficult to cure gastrointestinal cancers detected with these platforms because they are often discovered at the progressive state. Moreover, the majority of the symptoms associated with gastrointestinal cancers do not manifest themselves until late in their development. Accordingly, the performance status of patients with gastrointestinal cancers and their overall prognosis needs to be improved.

For example, although screening programs for colorectal cancer have become more prevalent and survival rates have gone up within last 30 years, only around 40-44% of the cancers are detected in an early, localized stage, likely due to the lack of sensitivity of most of these screening programs. The general recommendation both in the U.S. and Europe is that individuals with average risk for colorectal cancer start regular screening either with colonoscopy or fecal blood test at the age of 50. However, the cancer incidence is increasing also among younger adults.

Understanding alterations in metabolic profiles in the colon that occur with tumor onset and progression could lead to better diagnostic tests as well as uncover new approaches for treatment or even prevention of CRC. Most CRCs are believed to originate from adenomatous polyps that acquire distinct mutations and accumulate other molecular alterations that allow them to progress through distinct histopathologic stages before becoming invasive carcinomas. Some adenomatous polyps do not progress to invasive tumors. Thus, the availability of a metabolic fingerprint that could distinguish a polyp that is likely to progress from one that will not progress could guide the frequency of screening colonoscopies and other preventative measures.

Metabolomics, which is understood as the quantitative measurement of all (or a certain percentage of all, e.g., most) low-molecular-weight metabolites in an organism at a specified time under specific environmental conditions, has been shown to be an effective tool for disease diagnosis, biomarker screening, and characterization of biological pathways.

Metabolites are the end products of cellular processes and their concentrations reflect the functional status of the organism and thus they are closely related to the observed phenotype. Perturbations in biological pathways can amplify the concentration changes of metabolites, making small molecule metabolites very attractive biomarkers of disease detection.

Altered metabolism is a cancer hallmark, resulting from changes in signaling pathways, protein expression, and other molecular mechanisms. Altered metabolism also reflects specific biochemical adaptations during carcinogenesis, which may confer malignant cells' survival advantages.

Two of the most prominent technologies for metabolite detection and quantification are nuclear magnetic resonance (NMR) and mass spectrometry (e.g., coupled to liquid chromatograph-LC-MS, gas chromatograph-GC-MS or direct analysis-DESI, DART). Both NMS and MS technologies are widely used in research and clinical settings.

Mass spectrometry is essentially a technique for "weighing" molecules. It is based upon the motion of charged particles, called ions, in an electric or magnetic field. The mass to charge ratio (m/z) of a particular ion affects this motion. Since the charge of an electron is known, then the mass to charge ratio is a measurement of an ion's mass. Mass spectrometry allows scanning for a wide range of metabolites. Data can include several thousands of detected metabolic events and thus creates a large pool for potential biomarker selection.

Several challenges exist in applying mass spectrometry measurements of metabolites and lipids in order to identify the presence or risk of colorectal cancer and/or adenomatous polyps in a subject.

First, the sensitivity of mass spectrometry instrumentation has only recently, over the past 5 years, become sufficient to enable global profiling of different biomaterials. Accordingly, metabolite based diagnostics that look into the whole human metabolon are still in their developmental infancy.

Secondly, accurate measurements of metabolites generally requires an internal standard for each marker of interest. Such standards for metabolites may not commercially available, and accordingly must be synthesized. Accordingly, performing accurate measurements of metabolites requires significantly more than just measuring a given metabolite. The additional step and capability of synthesizing an internal standard is required.

Another challenge to the use of metabolite and lipid based biomarker detection is the sensitivity of metabolomics to population differences (e.g. population bias). Although metabolite profiles/fingerprints have the potential to act as indicators of disease, they are also very sensitive to minor differences in the biological background, and therefore also vary significantly across different populations. Therefore, a challenge in metabolomics based diagnostics is finding a method that is sensitive to the disease of interest, while at the same time robust to variations across e.g. different populations.

Likewise, metabolites and lipids are quite sensitive molecules to the pre-analytical treatment of a sample, including sample collection method, storage conditions, and other preparation steps. As a result, measurements of metabolites and lipids are influenced by, e.g. hemolysis, lipemia, sample time at room temperature before serum extraction and freezing, and the freeze-thaw cycles applied to the samples. Accordingly, sample collection and preparation methods that comprise appropriate quality controls and/or yield consistent measurements of target biomarkers must be developed and employed.

There is a need for diagnostics to identify the presence, stage, and/or risk of colorectal cancer and/or adenomatous polyps in a subject. Metabolomics and mass spectrometry based diagnostics is a promising approach, but requires identifying an appropriate panel of markers that are sensitive to the presence of colorectal cancer and/or adenomatous polyps in a subject, while at the same time robust to population variations, such as e.g. gender, age, ethnicity. Additionally, appropriate internal standards, and sample handling and quality control methods that enable accurate and reliable measurements are required.

SUMMARY

Described herein are sets of metabolite and lipid (e.g., fatty acid) markers that can be used in the detection of early stage colorectal cancer and/or early development of adenomatous polyps. Presented herein are illustrative pathology-linked panels. In certain embodiments, the markers presented herein (or subsets thereof) are used as a panel for detecting either colorectal cancer or adenomatous polyps at the same time. The markers presented herein include metabolites and lipids (e.g., fatty acids) freely detectable and accurately quantifiable in human serum. In certain embodiments, the sample may be plasma, urine, saliva, whole blood, dried blood spot or dried serum spot.

Also disclosed herein are methods and systems for improved sample handling and quality control.

In one aspect, the disclosed technology is direct to a method comprising: measuring, by mass spectrometry, a level of each of a plurality of species in a biological sample obtained from a human subject, wherein each of the plurality of species is at least one of a metabolite and a lipid (e.g., a fatty acid) and the plurality of species comprises:

determining a ratio of the measured level of PUFA 446 and the measured level of S192; and determining at least one of a presence of, a stage of, and a risk of colorectal cancer in the human subject based, at least in part, on the ratio of the measured level of PUFA 446 and the measured level of S192.

In certain embodiments, the plurality of species comprises one or more members in addition to PUFA 446 and S192 selected from the group consisting of the species listed in Table 12 and Table 13. In certain embodiments, the plurality of species comprises all of the species listed in Table 12 and 13 and the method comprises: determining at least one of a presence of, a stage of, and a risk of colorectal cancer in the human subject based, at least in part, on measured values for the ratios of species listed in Table 12; and determining at least one of a presence of, a stage of, and a risk of adenomatous polyps in the human subject based, at least in part, on measured values for the ratios of species listed in Table 13.

In certain embodiments, the measuring step comprises measuring the level of each of the plurality of species using a LC-MS, GC-MS, DESI, or DART technique.

In certain embodiments, the method comprises: determining at least one of a presence of, a risk of, and a stage of colorectal cancer based, at least in part, on a ratio of the measured value of a polyunsaturated fatty acid and the measured value of another of the plurality of species being lower than a representative ratio for a control population. In certain embodiments, the polyunsaturated fatty acid is a species listed in FIG. 1.

In certain embodiments, the method comprises: determining at least one of a presence of, a risk of, and a stage of colorectal cancer based, at least in part, on a ratio of the measured value of choline (S49) and the measured value of N1,N12-diacetylsperimne (S236) being lower than a representative ratio for a control population.

In certain embodiments, at least one of the plurality of species is selected from the group consisting of:

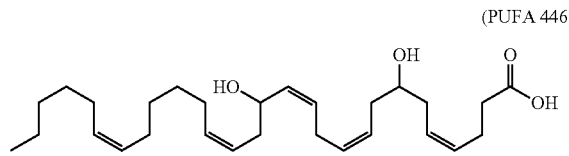
(PUFA 446)

and 3Me-glutaryl carnitine

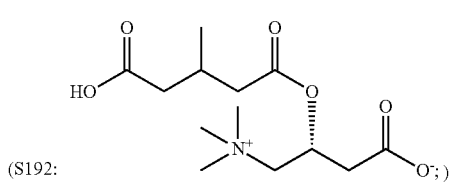
(S192:)

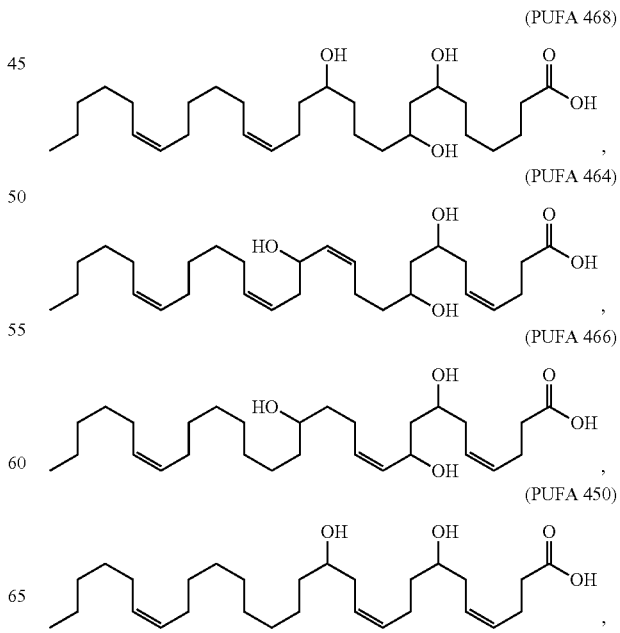
(PUFA 468)
(PUFA 464)
(PUFA 466)
(PUFA 450)

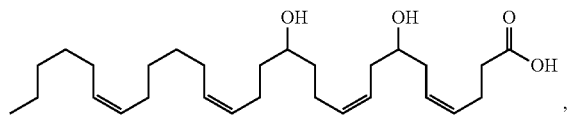
(PUFA 448)

In certain embodiments, the biological sample comprises serum. In certain embodiments, the biological sample is serum, plasma, urine, saliva, whole blood, a dried blood spot, or a dried serum spot.

In certain embodiments, the method comprises introducing at least a portion of the biological sample into a C18 50 mm column, a C18 100 mm column, or an amide column to determine a quantification of metabolites, lipids or polar metabolic compounds, respectively, of the plurality of species. In certain embodiments, the method comprises introducing at least a portion of the biological sample into a mass spectrometer by FIA based direct infusion injection to measure the level of a polyunsaturated fatty acid (e.g., in a semi-quantitative way). In certain embodiments, the method comprises measuring a stable isotopically labeled reference standard.

In one aspect, the disclosed technology is directed to a method comprising: measuring, by mass spectrometry, a level of each of a plurality of species in a biological sample obtained from a human subject, wherein each of the plurality of species is at least one of a metabolite and a lipid (e.g., a fatty acid) and the plurality of species comprises α-linolenic acid

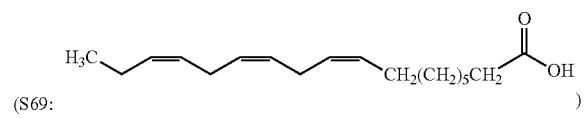
(S69: )

and L-cysteine S-sulfate

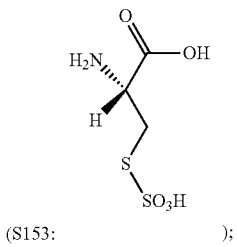 [SMILES: N[C@@H](CSS(=O)(=O)O)C(=O)O]
(S153: );

determining a ratio of the measured level of S69 and the measured level of S153; and determining at least one of a presence of, a stage of, and a risk of adenomatous polyps in the human subject based, at least in part, on the ratio of the measured level of S69 and the measured level of S153.

In certain embodiments, the method comprises: determining at least one of a presence of, a risk of, and a stage of adenomatous polyps based, at least in part, on a ratio of the measured value of a species in the plurality of species and the measured value of S153 or hippuric acid (S63) being higher than a representative ratio for a control population. In certain embodiments, the species in the plurality of species is octanoylcarnitine (AC 8:0) (S109), aspartylphenylalanine (S227), or S69.

In certain embodiments, the method comprises: determining at least one of a presence of, a risk of, and a stage of adenomatous polyps based, at least in part, on the measured level of S153 being lower than a representative level for a control population.

In certain embodiments, the biological sample comprises serum. In certain embodiments, the biological sample is serum, plasma, urine, saliva, whole blood, a dried blood spot, or a dried serum spot.

In certain embodiments, the method comprises: introducing at least a portion of the biological sample into a C18 50 mm column, a C18 100 mm column, or an amide column to determine a quantification of metabolites, lipids or polar metabolic compounds, respectively, of the plurality of species. In certain embodiments, the method comprises: introducing at least a portion of the biological sample into a mass spectrometer by FIA based direct infusion injection to measure the level of a polyunsaturated fatty acid (e.g., in a semi-quantitative way). In certain embodiments, the method comprises measuring a stable isotopically labeled reference standard.

In certain embodiments, the method comprises comparing certain metabolite ratios calculated for colorectal cancer and/or adenomatous polyp patients to a representative ratio for a control population.

In certain embodiments, the biological sample is obtained from the human subject by collecting blood from the subject when the subject is seated in an upright position, into evacuated blood collection tubes with no anticoagulant and leaving the blood to clot. In certain embodiments, methods comprise: checking the biological sample for hemolysis and/or lipemia prior to the measuring step; and excluding samples that have undergone lipemia and/or hemolysis. In certain embodiments, methods comprise measuring a level of a species in the biological sample that is indicative of a length of time the biological sample was kept at room temperature; and determining the length of time the biological sample was kept at room temperature.

It is contemplated that limitations presented with reference to a particular aspect of the invention may, in certain embodiments, be applicable to another aspect of the invention.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": As used herein, the term "administration" refers to the administration of a composition to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (including by intratracheal instillation), transdermal, vaginal and vitreal. In some embodiments, administration may involve intermittent dosing. In some embodiments, administration may involve continuous dosing (e.g., perfusion) for at least a selected period of time. As is known in the art, antibody therapy is commonly administered parenterally (e.g., by intravenous or subcutaneous injection).

"Biological Sample": As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

"Biomarker": The term "biomarker" is used herein, consistent with its use in the art, to refer to a to an entity whose presence, level, or form, correlates with a particular biological event or state of interest, so that it is considered to be a "marker" of that event or state. To give but a few examples, in some embodiments, a biomarker may be or comprises a marker for a particular disease state, or for likelihood that a particular disease, disorder or condition may develop. In some embodiments, a biomarker may be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic, of the relevant biological event or state of interest. A biomarker may be an entity of any chemical class. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is found outside of cells (e.g., is secreted or is otherwise generated or present outside of cells, e.g., in a body fluid such as blood, urine, tears, saliva, cerebrospinal fluid, etc.

"Biomolecule": As used herein, "biomolecule" refers to bioactive, diagnostic, and prophylactic molecules. Biomolecules that can be used in the present invention include, but are not limited to, synthetic, recombinant or isolated peptides and proteins such as antibodies and antigens, receptor ligands, enzymes, and adhesion peptides; nucleotides and polynucleic acids such as DNA and antisense nucleic acid molecule; activated sugars and polysaccharides; bacteria; viruses; and chemical drugs such as antibiotics, anti-inflammatories, and antifungal agents.

"Blood component": As used herein, "blood component" refers to any component of whole blood, including red blood cells, white blood cells, platelets, endothelial cells, mesothelial cells or epithelial cells. Blood components also include the components of plasma, such as proteins, metabolites, lipids, nucleic acids, and carbohydrates, and any other cells that can be present in blood, due to pregnancy, organ transplant, infection, injury, or disease.

"Cancer": The terms "cancer", "malignancy", "neoplasm", "tumor", and "carcinoma", are used interchangeably herein to refer to cells that exhibit relatively abnormal, uncontrolled, and/or autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. The teachings of the present disclosure may be relevant to any and all cancers. To give but a few, non-limiting examples, in some embodiments, teachings of the present disclosure are applied to one or more cancers such as, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

"Comparable": As used herein, the term "comparable" refers to two or more agents, entities, situations, sets of conditions, etc., that may not be identical to one another but that are sufficiently similar to permit comparison there between so that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc., to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

"Diagnostic information": As used herein, "diagnostic information" or "information for use in diagnosis" is information that is useful in determining whether a patient has a disease, disorder or condition and/or in classifying a disease, disorder or condition into a phenotypic category or any category having significance with regard to prognosis of a disease, disorder or condition, or likely response to treatment (either treatment in general or any particular treatment) of a disease, disorder or condition. Similarly, "diagnosis" refers to providing any type of diagnostic information, including, but not limited to, whether a subject is likely to have or develop a disease, disorder or condition, state, staging or characteristic of a disease, disorder or condition as manifested in the subject, information related to the nature or classification of a tumor, information related to prognosis and/or information useful in selecting an appropriate treatment. Selection of treatment may include the choice of a particular therapeutic agent or other treatment modality such as surgery, radiation, etc., a choice about whether to withhold or deliver therapy, a choice relating to dosing regimen (e.g., frequency or level of one or more doses of a particular therapeutic agent or combination of therapeutic agents), etc.

"Marker": A marker, as used herein, refers to an entity or moiety whose presence or level is a characteristic of a particular state or event. In some embodiments, presence or level of a particular marker may be characteristic of presence or stage of a disease, disorder, or condition. To give but one example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy. A marker may be a metabolite, lipid, fatty acid, and/or polyunsaturated fatty acid. In certain embodiments, the term marker may refer to a ratio of two entities (e.g., moieties).

"Prevent or prevention": as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

"Prognostic and predictive information": As used herein, the terms "prognostic information" and "predictive information" are used to refer to any information that may be used to indicate any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

"Prevention": The term "prevention", as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. Prevention may be considered complete when onset of a disease, disorder or condition has been delayed for a predefined period of time.

"Ratio": As used herein, the term "ratio" refers to a calculable relationship used to compare amounts of two species that indicates the relative amounts of the species. The species may be markers, such as metabolites and/or lipids (e.g., fatty acids), for example. A ratio may be a direct proportion or inverse proportion (e.g., a first amount divided by a second amount or the second amount divided by the first amount, respectively). A ratio may be weighted and/or normalized (either the numerator, the denominator, or both). The two amounts may be physical quantities or arbitrary values that correspond to physical quantities. For example, a ratio may be calculated from two intensity amounts (i.e., in arbitrary units) in two species (e.g., markers) measured by a mass spectrometry technique.

"Reference": As used herein, the term "reference" describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

"Risk": as will be understood from context, "risk" of a disease, disorder, and/or condition comprises likelihood that a particular individual will develop a disease, disorder, and/or condition (e.g., a radiation injury). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., a radiation injury). In some embodiments a reference sample or group of reference samples are from individuals comparable to a particular individual. In some embodiments, relative risk is 0, 1, 2, 3, 4, 5, 6, 7, 8, 9, 10, or more.

"Sample": As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid; peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

"Small molecule": As used herein, the term "small molecule" means a low molecular weight organic and/or inorganic compound. In general, a "small molecule" is a molecule that is less than about 5 kilo-Daltons (kD) in size. In some embodiments, a small molecule is less than about 4 kD, 3 kD, about 2 kD, or about 1 kD. In some embodiments, the small molecule is less than about 800 Daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., comprises at least one detectable moiety). In some embodiments, a small molecule is a therapeutic. Those of ordinary skill in the art, reading the present disclosure, will appreciate that certain small molecule compounds described herein may be provided and/or utilized in any of a variety of forms such as, for example, salt forms, protected forms, pro-drug forms, ester forms, isomeric forms (e.g., optical and/or structural isomers), isotopic forms, etc. In some embodiments, reference to a particular compound may relate to a specific form of that compound. In some embodiments, reference to a particular compound may relate to that compound in any form. In some embodiments, where a compound is one that exists or is found in nature, that compound may be provided and/or utilized in accordance in the present invention in a form different from that in which it exists or is found in nature. Those of ordinary skill in the art will appreciate that a compound preparation including a different level, amount, or ratio of one or more individual forms than a reference preparation or source (e.g., a natural source) of the compound may be considered to be a different form of the compound as described herein. Thus, in some embodiments, for example, a preparation of a single stereoisomer of a compound may be considered to be a different form of the compound than a racemic mixture of the compound; a particular salt of a compound may be considered to be a different form from another salt form of the compound; a preparation containing one conformational isomer ((Z) or (E)) of a double bond may be considered to be a different form from one containing the other conformational isomer ((E) or (Z)) of the double bond; a preparation in which one or more atoms is a different isotope than is present in a reference preparation may be considered to be a different form; etc.

"Subject": As used herein, the term "subject" includes humans and mammals (e.g., mice, rats, pigs, cats, dogs, and horses). In many embodiments, subjects are be mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Substantially": As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Susceptible to": An individual who is "susceptible to" a disease, disorder, or condition (e.g., influenza) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from the disease, disorder, or condition).

"Treatment": As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment can be of a subject who does not exhibit signs of the relevant disease, disorder and/or condition and/or of a subject who exhibits only early signs of the disease, disorder, and/or condition. Alternatively or additionally, such treatment can be of a subject who exhibits one or more established signs of the relevant disease, disorder and/or condition. In some embodiments, treatment can be of a subject who has been diagnosed as suffering from the relevant disease, disorder, and/or condition. In some embodiments, treatment can be of a subject known to have one or more susceptibility factors that are statistically correlated with increased risk of development of the relevant disease, disorder, and/or condition.

"Early stage": As used herein, the term "early stage" refers to a localized stage where cancer has not yet spread to nearby lymph nodes (NO) or to distant sites (MO). For example, pathologically it would be cancer stages from stage 0 to stage II C.

Drawings are presented herein for illustration purposes, not for limitation.

BRIEF DESCRIPTION OF THE DRAWINGS

Drawings are presented herein for illustration purposes, not for limitation. The patent or application file contains at least one drawing executed in color. Copies of this patent or patent application publication with color drawing(s) will be provided by the Office upon request and payment of the necessary fee. The foregoing and other objects, aspects, features, and advantages of the invention will become more apparent and may be better understood by referring to the following description taken in conjunction with the accompanying drawings, in which.

DETAILED DESCRIPTION

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions can be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim. Headers are provided for the convenience of the reader and are not intended to be limiting with respect to the claimed subject matter.

Marker Panel, and Classification Approach

Described herein are sets of metabolite and lipid markers that can be used as a full panel or as a subset of markers for early stage colorectal cancer and early development of adenomatous polyp detection. In certain embodiments, these markers (or subsets thereof) are separated into pathology-linked panels. In certain embodiments, these markers (or subsets thereof) are used as a single panel for detecting both colorectal cancer and adenomatous polyps at the same time. In certain embodiments, these markers are metabolites and lipids (e.g., fatty acids) freely detectable and accurately quantifiable in human serum. In certain embodiments, the sample may be plasma, urine, saliva, whole blood, dried blood spot or dried serum spot.

In certain embodiments, markers are measured using mass spectrometry. In some embodiments, markers are measured using column-based liquid-chromatography mass spectrometry (LC-MS). For example, a C18 50 mm column may be used for metabolite quantification (e.g. using an AB Sciex TQ mass spectrometer). Alternatively, an Amide column may be used for detecting polar metabolic compounds (e.g. using an AB Sciex TQ mass spectrometer). For example, an ACQUITY UPLC BEH C18 Column, 130 Å, 1.7 μm, 2.1 mm×50 mm may be used for metabolite quantification. Alternatively, an ACQUITY UPLC BEH Amide Column, 130 Å, 1.7 μm, 2.1 mm×150 mm may be used for detecting polar metabolic compounds. A C18 100 mm column may be used for lipid quantification (e.g. using an AB Sciex QTRAP). In some embodiments, detection of species uses direct injection methods, for example, FIA based direct injection for analyzing fatty acids (e.g. poly-unsaturated fatty acids (PUFA)) (e.g. using an AB Sciex QTRAP).

Figure 1:
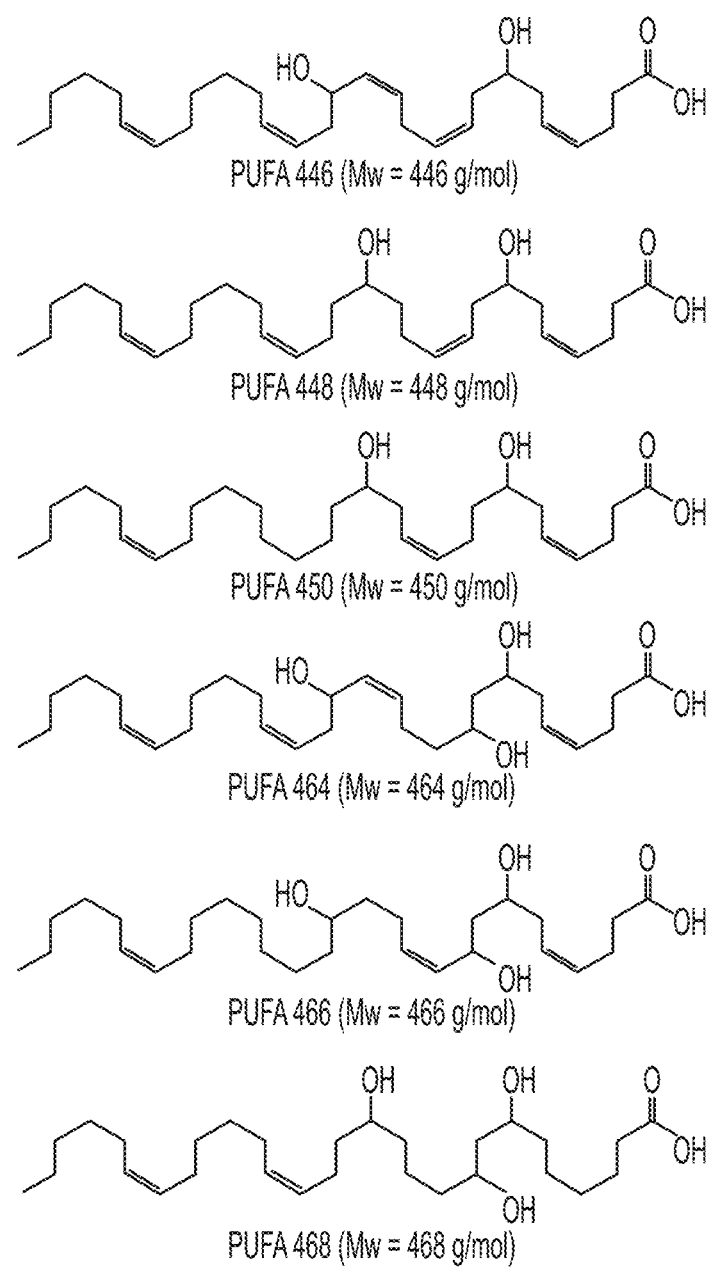
FIG. 1 shows the chemical structure of 6 PUFA (polyunsaturated fatty acid) molecules.
Figure 2:
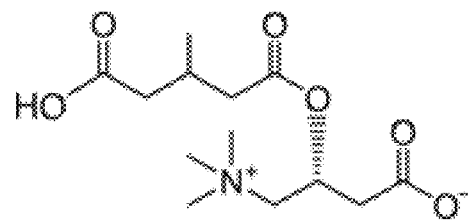
FIG. 2 shows chemical structures of α-linolenic acid, 3Me-Glutaryl Carnitine, L-cysteine S-Sulfate.
Figure 2:
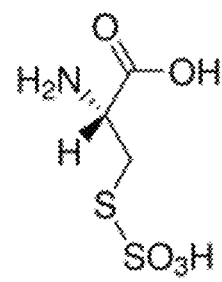
Figure 2:
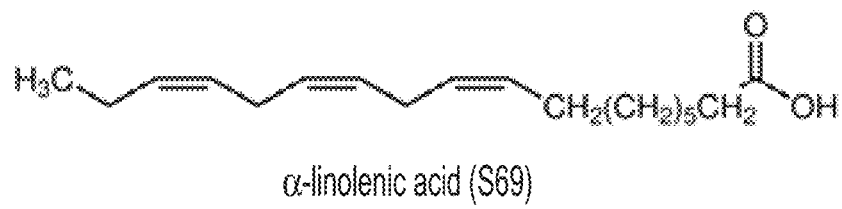

The panel of markers shown in Table 1 and Table 2 was identified using an exemplary assay development process described herein. Table 1 lists the names of the different markers, along with the detection method used to measure each marker ("Column" heading in the table). Certain markers may be measured by more than one different method. Chemical structures of several of the molecules are shown in FIG. 1 and FIG. 2. In certain embodiments, the molecules represented in FIG. 1 and FIG. 2 are used as or in markers in a panel for diagnosing colorectal cancer and/or adenomatous polyps. FIG. 1 Referring now to FIG. 1, the six polyunsaturated fatty acids represented in the figure are labeled according to their molecular weight for ease in distinguishing between species and (e.g., "PUFA 446" corresponds to the polyunsaturated fatty acid represented in FIG. 1 having molecular weight of 446 g/mol).

TABLE 1

Listing of species identified

| Lab code | Name | Column |
|---|---|---|
|  | 1-(1-enyl-stearoyl)-GPE (P-18:0)* | Amide |
| S261 | Alanine | Amide |
| S49 | CHOLINE | Amide |
| S325 | glycerophosphoethanolamine (GPE-2) | Amide |
| S153 | L-cysteine S-sulfate | Amide |
| S110 | L-Histidine | Amide |
| S125 | L-Lysine | Amide |
| S132 | L-proline | Amide |
| S236 | N1,N12-Diacetylspermine | Amide |
| S111 | NG,NG-dimethylarginine (asym) (ADMA) | Amide |
| S78 | NICOTINAMIDE | Amide |
| S179 | sn-Glycero-3-phosphocholine | Amide |
| S175 | 1,18-Octadecanedicarboxylic acid | C18 |
| S3 | 14:0 Lyso PC | C18 |
| S15 | 16:0 Lyso PC | C18 |
| S103 | 1-Methyladenosine | C18 |
| S105 | 1-O-Palmityl-sn-glycero-3-phosphocholine | C18 |
| S193 | 2-D-Mannopyranosyl-L-tryptophan | C18 |
| S305 | 3-(3-hydroxyphenyl)propionate | C18 |
| S192 | 3Me-Glutaryl Carnitine | C18 |
| S285 | Acetoacetate | C18 |
| S227 | Aspartylphenylalanine | C18 |
| S295 | Azelaic acid | C18 |
| S168 | Delta-Valerolactam | C18 |
| S62 | GLYCOCHOLIC ACID | C18 |
| S52 | GLYCODEOXYCHOLATE | C18 |
| S63 | HIPPURIC ACID | C18 |
| S65 | KYNURENIC ACID | C18 |

TABLE 1-continued

Listing of species identified

| Lab code | Name | Column |
|---|---|---|
| S69 | α-LINOLENIC ACID | C18 |
| S150 | L-Pyrogutamic acid | C18 |
| S1 | L-Tryptophan | C18 |
| S100 | L-tyrosine | C18 |
| S133 | Lyso PC 18:0 | C18 |
| S126 | Lyso PC 20:0 | C18 |
| S171 | N-(2-Furoyl)glycine | C18 |
| S166 | N-Acetylcytidine | C18 |
| S76 | N-ACETYLGLYCINE | C18 |
| S170 | Nonanoic Acid | C18 |
| S109 | Octanoylcarnitine (AC 8:0) | C18 |
| S147 | Propionyl L-carnitine (AC 3:0) | C18 |
| S10 | Sebacic acid | C18 |
| S94 | XANTHUNERIC ACID | C18 |
| S176 | y-cehc | C18 |
| PUFA6 | PUFA 468 | C18-100 mm |
|  | AC 4:0 | C18-100 mm |
|  | AC 14:0 | C18-100 mm |
|  | AC 16:0 | C18-100 mm |
|  | LPA 16:0 | C18-100 mm |
|  | LPC 18:2 | C18-100 mm |
|  | LPC 20:3 | C18-100 mm |
|  | LPC O-16:0 | C18-100 mm |
|  | LPE 18:2 | C18-100 mm |
|  | LPI 18:0 | C18-100 mm |
|  | LPI 18:1 | C18-100 mm |
|  | LPI 20:3 | C18-100 mm |
|  | PC 34:2 (16:1_18:1) | C18-100 mm |
|  | PC 36:1 | C18-100 mm |
|  | PC 36:1 (18:1_18:0) | C18-100 mm |
|  | PC 36:4 (18:2/18:2) | C18-100 mm |
|  | PC 36:4 (16:0/20:4) | C18-100 mm |
|  | PC 38:5 | C18-100 mm |
|  | PC 38:5 (16:0/22:5) | C18-100 mm |
|  | PC 38:5 (18:2/20:3) | C18-100 mm |
|  | PC 38:6 (18:2/20:4) | C18-100 mm |
|  | PC 40:4 (18:0/22:4) | C18-100 mm |
|  | PC O-34:2 (16:0/18:2) | C18-100 mm |
|  | PC O-34:3 | C18-100 mm |
|  | PC O-36:3 | C18-100 mm |
|  | PC O-36:4 (16:0/20:4) | C18-100 mm |
|  | PC O-38:4 | C18-100 mm |
|  | PC O-40:1 | C18-100 mm |
|  | PC O-42:1 | C18-100 mm |
|  | PC O-44:4 | C18-100 mm |
|  | PI 36:3 (18:1/18:2) | C18-100 mm |
|  | PI 36:1 (18:0/18:1) | C18-100 mm |
|  | PI 36:2 (18:1/18:1) | C18-100 mm |
| S18 | S1P (Spingosine 1-P) | C18-100 mm |
|  | SM 38:0 | C18-100 mm |
| PUFA1 | PUFA 446 | FIA |
| PUFA2 | PUFA 448 | FIA |
| PUFA3 | PUFA 450 | FIA |
| PUFA4 | PUFA 464 | FIA |
| PUFA5 | PUFA 466 | FIA |
| PUFA6 | PUFA 468 | FIA |

TABLE 2

Listing of markers, along with indications of which markers may be interchanged with each other, or used as quality controls. Several markers in addition to those listed in Table 1 are also included

| UDX Code | Name of the Molecule | Method of Detection | Comments |
|---|---|---|---|
|  | 1-(1-enyl-stearoyl)-GPE (P-18:0)* | Amide | Putative identification |
| S261 | Alanine | Amide |  |
| S49 | CHOLINE | Amide |  |
| S325 | Glycerophosphoethanolamine (GPE-2) | Amide |  |
| S153 | L-cysteine S-Sulfate | Amide |  |
| S110 | L-Histidine | Amide | Can be interchanged with S236 |

TABLE 2-continued

Listing of markers, along with indications of which markers may be interchanged with each other, or used as quality controls. Several markers in addition to those listed in Table 1 are also included

| UDX Code | Name of the Molecule | Method of Detection | Comments |
|---|---|---|---|
| S125 | L-Lysine | Amide | |
| S132 | L-proline | Amide | |
| S236 | N1,N12-Diacetylspermine | Amide | |
| S111 | NG,NG-dimethylarginine (asym) (ADMA) | Amide | |
| S78 | NICOTINAMIDE | Amide | |
| S179 | Sn-Glycero-3-phosphocholine | Amide | |
| S175 | 1,18-Octadecanedicarboxylic acid | C18 | |
| S3 | 14:0 Lyso PC | C18 | Can be interchanged with S15, S126, S133, LPC 20:3 |
| S15 | 16:0 Lyso PC | C18 | Can be interchanged with S3, S126, S133 |
| S103 | 1-Methyladenosine | C18 | Can be interchanged with S166 |
| S105 | 1-O-Palmityl-sn-glycero-3-phosphocholine | C18 | |
| S193 | 2-D-Mannopyranosyl-L-tryptophan | C18 | |
| S305 | 3-(3-hydroxyphenyl)propionate | C18 | |
| S192 | 3Me-Glutaryl Carnitine | C18 | |
| S285 | Acetoacetate | C18 | |
| S227 | Aspartylphenylalanine | C18 | |
| S295 | Azelaic acid | C18 | Too low concentration (may be excluded from the panel entirely) |
| S168 | Delta-Valerolactam | C18 | Can be interchanged with S176 |
| S61 | GLYCOCHENODEOXYCHOLATE | C18 | Marker used for evaluating icterus |
| S62 | GLYCOCHOLIC ACID | C18 | Marker used for evaluating icterus |
| S52 | GLYCODEOXYCHOLATE | C18 | Marker used for evaluating icterus |
| S63 | HIPPURIC ACID | C18 | |
| S65 | KYNURENIC ACID | C18 | Linked to S1 and S94 |
| S69 | LINOLENIC ACID | C18 | |
| S150 | L-Pyroqutamic acid | C18 | Marker indicating time at room temperature |
| S1 | L-Tryptophan | C18 | Can be interchanged with S94 |
| S100 | L-tyrosine | C18 | |
| S133 | Lyso PC 18:0 | C18 | Can be interchanged with S3, S126, S133 |
| S126 | Lyso PC 20:0 | C18 | Can be interchanged with S3, S126, S133 |
| S171 | N-(2-Furoyl)glycine | C18 | Can be interchanged with S170 |
| S166 | N-Acetylcytidine | C18 | Can be interchanged with S103 |
| S76 | N-ACETYLGLYCINE | C18 | |
| S170 | Nonanoic Acid | C18 | Can be interchanged with S171 |
| S109 | Octanoylcarnitine (AC 8:0) | C18 | |
| S147 | Propionyl L-carnitine (AC 3:0) | C18 | |
| S10 | Sebacic acid | C18 | Marker indicating improper sample collection |
| S94 | XANTHUNERIC ACID | C18 | |
| S176 | y-cehc | C18 | Can be interchanged with S168 |
| S313 | N2,N2-dimethylguanosine | C18 | |
| S321 | DSGEGDFXAEGGGVR * (Androsterone sulfate | C18 | |
| S333 | N2-methylguanosine | C18 | |
| | PUFA468 | C18-100 mm | |
| S245 | AC 4:0 | C18-100 mm | |
| | LPA 16:0 | C18-100 mm | |
| | LPC 18:2 | C18-100 mm | Can be interchanged with LPE 18:2 |
| | LPC 20:3 | C18-100 mm | Can be interchanged with S3 |
| | LPC O-16:0 | C18-100 mm | Can be interchanged with S3 |
| | LPE 18:2 | C18-100 mm | Can be interchanged with LPC 18:2 |

TABLE 2-continued

Listing of markers, along with indications of which markers may be interchanged with each other, or used as quality controls. Several markers in addition to those listed in Table 1 are also included

| UDX Code | Name of the Molecule | Method of Detection | Comments |
|---|---|---|---|
| S341 | LPI 18:0 | C18-100 mm | Can be interchanged with LPI 18:1 |
|  | LPI 18:1 | C18-100 mm |  |
|  | LPI 20:3 | C18-100 mm |  |
|  | PC 34:2 (16:1_18:1) | C18-100 mm |  |
|  | PC 36:1 (18:1/18:0) | C18-100 mm |  |
|  | PC 36:1 (18:1_18:0) | C18-100 mm |  |
| S338 | PC 36:4 (18:2/18:2) | C18-100 mm | Can be interchanged with PC 38:6 (18:2/20:4) |
| S339 | PC 36:4 (16:0/20:4) | C18-100 mm |  |
|  | PC 38:5 (20:4/18:1) | C18-100 mm |  |
|  | PC 38:5 (16:0/22:5) | C18-100 mm |  |
|  | PC 38:5 (18:2/20:3) | C18-100 mm |  |
|  | PC 38:6 (18:2/20:4) | C18-100 mm | Can be interchanged with PC 36:4 (18:2/18:2) |
|  | PC 40:4 (18:0/22:4) | C18-100 mm |  |
|  | PC O-34:2 (16:0/18:2) | C18-100 mm | Can be interchanged with PC O-36:3 (18:1/18:2) |
|  | PC O-34:3 | C18-100 mm |  |
|  | PC O-36:3 (18:1/18:2) | C18-100 mm | Can be interchanged with PC O-34:2 (16:0/18:2) |
|  | PC O-36:4 (16:0/20:4) | C18-100 mm |  |
|  | PC O-38:4 (18:0/20:4) | C18-100 mm |  |
|  | PC O-40:1 | C18-100 mm |  |
|  | PC O-42:1 | C18-100 mm |  |
|  | PC O-44:4 | C18-100 mm |  |
|  | PI 36:3 (18:1)/18:2) | C18-100 mm |  |
|  | PI 36:1 (18:0/18:1) | C18-100 mm | Can be interchanged with S329, PI 36:3 (18:1/18:2) |
| S329 | PI 36:2 (18:1/18:1) | C18-100 mm | Can be interchanged with PI 36:1 (18:0/18:1), PI 36:3 (18:1/18:2) |
| S18 | S1P (Spingosine 1-P) | C18-100 mm |  |
|  | SM 38:0 | C18-100 mm |  |
| S2 | Oleoyl L-Carnitine | C18-100 mm | Can be interchanged with S127, S135 |
|  | LPC 15:0 | C18-100 mm | Can be interchanged with LPC 18:1, LPC 20:2 |
|  | LPC 18:1 | C18-100 mm | Can be interchanged with LPC 15:0, LPC 18:1 |
|  | LPC 20:2 | C18-100 mm | Can be interchanged with LPC 15:0, LPC 18:1 |
|  | PC 42:8 | C18-100 mm |  |
|  | FFA 22:0 | C18-100 mm |  |
|  | PE(P-18:1/18:1) | C18-100 mm |  |
|  | PE(18:2/18:2) | C18-100 mm |  |
| S342 | PC 38:6 (16:0/22:6) | C18-100 mm |  |
| S135 | (±)-Myristoylcarnitine (AC 14:0) | C18-100 mm | Can be interchanged with S127, S2 |
| S127 | Palmitoyl-L-carnitine (AC 16:0) | C18-100 mm | Can be interchanged with S2, S135 |
|  | PUFA 446 | FIA | Can be interchanged with PUFA 468 |
|  | PUFA 448 | FIA |  |
|  | PUFA 450 | FIA |  |
|  | PUFA 464 | FIA |  |
|  | PUFA 466 | FIA |  |
|  | PUFA 468 | FIA | Can be interchanged with PUFA 446 |
|  | LFA 538 | FIA | Putative identification |
|  | LFA 592 | FIA | Putative identification |
|  | LFA 594 | FIA | Putative identification |

In certain embodiments, measurements of all or small subsets of (e.g., at least 2, at least 3, at least 4, at least 5, between 2 and 80, between 2 and 50, between 3 and 50, between 4 and 50, between 10 and 40, no greater than 80, no greater than 70, no greater than 60, no greater than 50, no greater than 40, no greater than 30, no greater than 20, e.g., 2, e.g., 3, e.g., 4, e.g., 10, e.g., 12, e.g. 16, e.g., 30 of) these markers may be used in a predictive model (e.g. based on statistical pattern recognition methods, such as, e.g. Naïve Bayes classifiers, Support Vector Machines (SVM), Random Forests (RF)) to distinguish between healthy and diseased states related to colorectal cancer. In certain other embodiments, an individual marker may be used in the predictive model. In certain embodiments, a patient or sample may be identified (e.g. classified) as having colorectal cancer or adenomatous polyp or either colorectal cancer or adenomatous polyp using the predictive model.

The development of a predictive model, or classifier, may follow the general two-step approach of (1) training, followed by (2) classification, or testing. The training step is used to build the predictive model using data (e.g. measurements of markers) that correspond to samples that are known to belong to specified classes, and creating a classifier on the basis of that known content that accurately identifies the class (e.g. positive or negative for colorectal cancer, adenomatous polyp) based on the values of measurements of a set of markers from the panel. As would be appreciated by one of skill in the art, this step may comprise a feature selection process, wherein the best markers are identified (e.g. an optimal set of a predefined number of markers). To find thresholds for given content, one needs to train the classifier with sample content that represents members of all of the classes. Training may be carried out on a portion (e.g. 70%) of the data.

In certain embodiments, the remaining portion of the data (e.g. 30%) may be used to test the classifier, by using the model to predict the health state of patients in the testing set. Since the real health status of each individual in the testing set is known, the accuracy of the model can be assessed by comparing the real classes with predicted classes.

This approach can be used to assess the performance of the classifier, by calculating e.g. true and false positive rates, as well as e.g. sensitivities (the true positive rate) and specificity (1—the false positive rate) based on particular cut of points for different variable parameters (e.g. cut-off thresholds for particular markers). Varying parameters may be used to generate standard Receiver Operating Characteristic (ROC) curves, which may plot the the true positive rate (TPR) against the false positive rate (FPR) at various threshold settings. The area under the ROC curve (AUC) is a measure of how well a parameter can distinguish between two diagnostic groups (e.g. disease versus normal).

Clinical predictive algorithms may also be adapted in such a way so that the mistake of classifying cancer patients as normal (false negative) is less likely than the mistake of classifying a healthy person as having cancer (false positive), or, vice versa—e.g., such that the mistake of a false positive is less likely than the mistake of a false negative.

Certain markers may be measured by multiple methods, such that each measurement may be used as an input to the predictive model (e.g. each measurement of a given species acts as a separate biomarker). For example, measuring PUFA 468 using a lipid quantification approach (e.g. using C18-100 mm column) as well as in FIA method has been found to adding additional statistical value to the panel.

Additionally, certain markers may be interchanged with each other (e.g. as a result of being highly correlated). For example, a predictive model that uses S3 (14:0 Lyso PC) as an input would perform similarly to one that uses S15, S126, or S133 in place of S3, but is otherwise identical. Table 2 lists which markers can be interchanged with others.

Certain markers may also be used in quality control measures, for example as indicators of sample handling and storage conditions as will be discussed herein. Table 2 also provides indications of these markers.

Several of the markers in Table 1 and Table 2 can be identified as belong to particular classes of molecules. The predictive value these markers provide for detecting colorectal cancer or polyps is therefore indicative of the potential predictive value of other molecules belonging to the same class. For example, the PUFA fatty acid group is especially indicative of colorectal cancer. The chemical structures of 6 relevant PUFAs are shown in FIG. 1. The drop in the concentration of these fatty acids is a clear indicator of strong risk of having colorectal cancer.

In certain embodiments, fatty acids, including the PUFA molecules in FIG. 1, represent an important category of markers for use in a diagnostic panel.

Markers related to phenylalanine may also represent an important class of markers.

Additionally, lipids from lysophospholipid class (LPC 14:0, LPC 16:0, LPC 18:2, LPC 20:0 and LPC 20:3) and phosphocholine class (PC 34:2 (16:1_18:1), PC 36:1, PC 36:1 (18:1_18:0), PC 36:4 (18:2/18:2), PC 36:4 (16:0/20:4), PC 38:5, PC 38:5 (16:0/22:5), PC 38:5 (18:2/20:3), PC 38:6 (18:2/20:4), PC 40:4 (18:0/22:4)) are especially indicative of colorectal cancer.

Triacylglycerides, phosphoglycerides (e.g. PC, PE, and PI molecules listed in Table 1), sterols, and sphingolipids also represent an important class of relevant biomarkers.

Another important class of molecules comprises acylcarnitines.

The carnitines, e.g. S147, AC 4:0, AC 14:0, AC 16:0, S192 and S109, are an important group of molecules especially for detecting adenomas.

Constituent amino acids of elastin, such as proline, leucine, valine and glycine may correspond to an important group of molecules for cancer detection.

In one embodiment, subsets of the markers identified in Table 1 and Table 2 were identified as providing distinguishable specific signatures that would work for 2 different classification problems. These are (i) colorectal cancer vs control, (ii) adenomatous polyp vs control. For both of (i)-(ii), a distinct set of markers to be measured as inputs to a predictive model was identified.

Check for Lack of Population Bias Experiment

Because of the challenge population bias presents in metabolomics, markers were checked for robustness to variations in age, gender and ethnicity. Markers that have tendency to be highly indicative of age or gender nor ethnicity may introduce bias into analysis algorithm and thus could potentially result with clinically invalid assay. Accordingly, in one embodiment, only markers that were robust to variations in age, gender and ethnicity were included.

Figure 4:
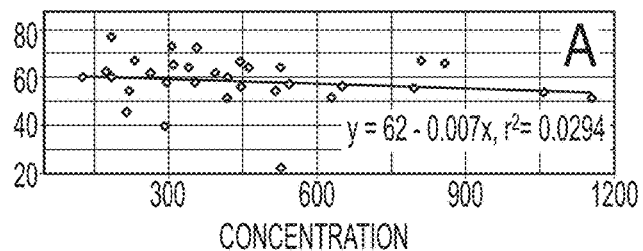
FIG. 4 shows a bias test performed on marker PUFA 468, wherein panel A represents an age versus concentration plot for control samples, panel B represents an age versus concentration plot for colorectal cancer patients, panel C represents an age versus concentration plot for adenomatous polyp patients, panel D represents box-plots for male patients, and panel E represents box-plots for female patients.
Figure 4:
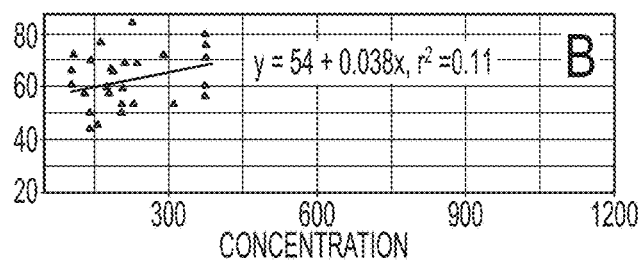
Figure 4:
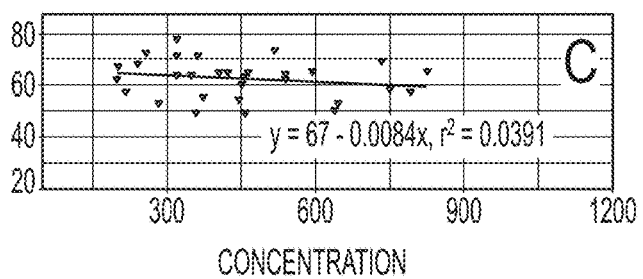
Figure 4:
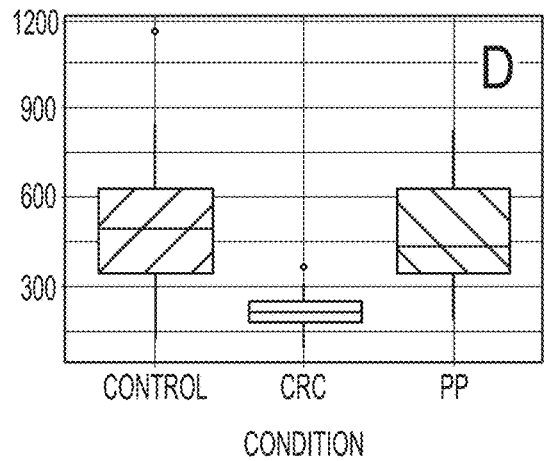
Figure 4:
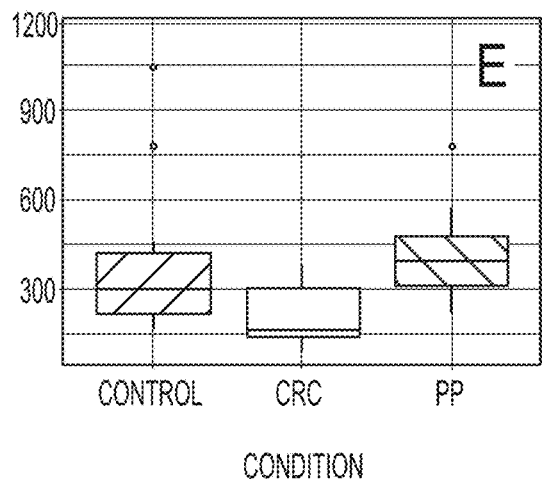

FIG. 4 shows results of an example of a test made on checking for age and gender bias for the PUFA 468 marker. Panels A-C show concentration values (given in arbitrary units) plotted against the age of the patients for control patients (panel A), patients with colorectal cancer (panel B), and patients with adenomatous polyps (panel C). A linear regression was used to determine the correlation between age and concentration by evaluating the $r^2$ coefficient. An $r^2$ value close to 1 is indicative of a strong correlation, while an $r^2$ coefficient close to 0 indicates no correlation. The highest observed $r^2$ value for the data in FIG. 4 is 0.11, which, without wishing to be bound by any theory, means that no age bias can be detected for the data presented in panels A-C. Panels D-E show box-plots of concentration values or male patients (panel D) and female patients (panel E). Both data sets present similar behavior of the PUFA 468 marker (e.g. a reduced concentration of the PUFA 468 molecule in patients having CRC), indicating a lack of gender bias.

Similar graphs have been generated for all markers. Markers with strong inclination to having bias were eliminated from consideration.

While the markers themselves do not have biological bias, it is still possible to include parameters such as age and gender as important parameters in a prediction algorithm as physiological markers.

Sample Preparation, Quality Control and Measurement Methods

In addition to population bias, as discussed herein, pre-analytical bias is another important consideration in metabolomics based diagnostics.

In order to address the challenge of pre-analytical bias, strict sample collection protocols and quality control methods may be employed.

In certain embodiments, sample handling methods that result in hemolysis, protein aggregation or contamination, should be avoided. For example, strong mechanical treatment that would cause red cell rupture should be avoided.

Exemplary Serum Sample Collection Protocol

The following is an exemplary serum sample collection protocol.

The following are provided for use in sample collection: VACUETTE® Serum Clot Activator Tubes with gel separator (red cap, yellow ring) (supplied by Greiner Bio-One); Matrix 1 mL 2D tube+cap, 1D side racked ST (supplied by Thermoscientific); and a thermometer/hygrometer.

The following equipment and supplies are required at the collection site: a pipette and disposable filter tips for serum handling (500 μL, into every matrix2D tubes); a refrigerated centrifuge capable of chilling to 4° C. and centrifuging at 2000×g; a refrigerated centrifuge capable of chilling to 4° C. and centrifuging at 16000×g; and an ultralow freezer capable of chilling to −80° C. (−112° F.).

First, an 8 mL of whole blood should be collected using provided tubes for serum separation. The tube should be inverted 5-10 times immediately after collection. After collecting 8 mL of whole blood using VACUETTE Serum Clot Activator Tubes and inverting, the blood should be left clotting for half an hour to 1 hour at room temperature. The tubes should be kept vertical while clotting. The temperature and humidity conditions should be registered during clotting using the provided thermometer/hygrometer.

After the clotting period, the blood should be centrifuged at 2000×g for 10 minutes at 4° C. (39.2° F.). The time at which sample is centrifuged should be registered. Next, a pipette with disposable filter tips is used to transfer serum supernatant obtained via centrifugation into provided Matrix2D tubes, divided into aliquots with 500 μL of serum in each. Great care needs to be taken when aliquoting the samples to not disturb the red blood cell pellet that forms during centrifugation. The last aliquot man have less than 500 μL. A different tip must be used for each patient and the pipette must be kept in a vertical position during the process in order to ensure accurate dispensing volume.

Figure 3:
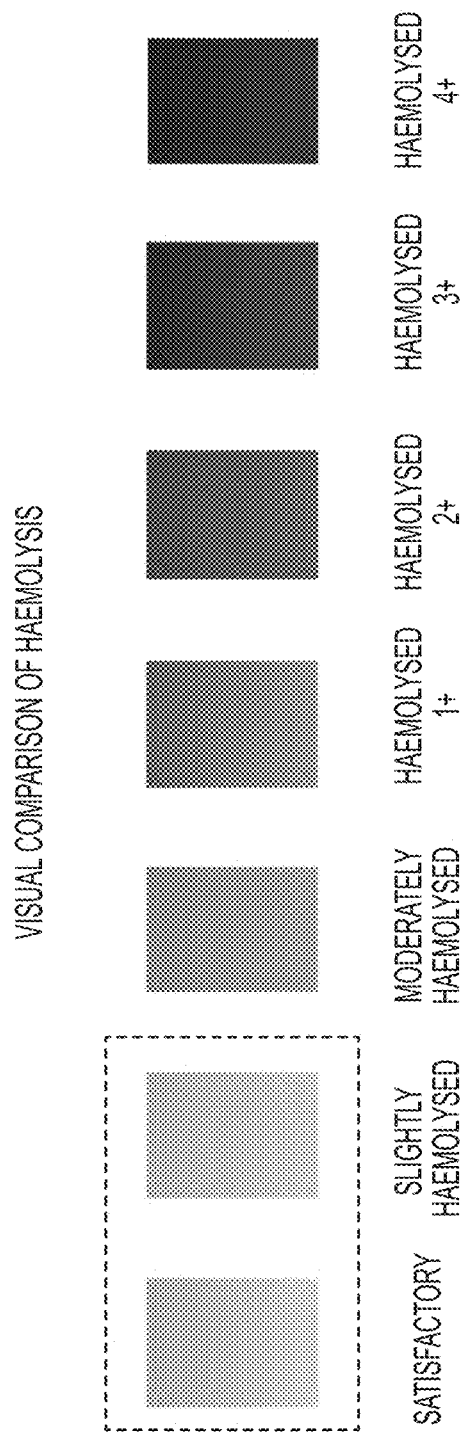
FIG. 3 shows a set of qualitative indicators that may be used for visual comparison to qualitative determine hemolysis in serum samples, according to an illustrative embodiment of the present invention.

The hemolysis level can be visually inspected during the serum sample collection process to ensure the collection of viable samples. Visibly hemolyzed samples are not acceptable for metabolomics studies and should be excluded. FIG. 3 shows a qualitative visual comparison guide that can be used to determine whether hemolysis has occurred in samples. The indicators inside the box in FIG. 3 (i.e., the two leftmost indicators) correspond to samples which are valid for use in further analysis. All aliquots should have similar coloring in order to ensure accurate and consistent analysis results. In certain embodiments, collected samples can be stored at room temperature for up to two weeks after collection. In certain embodiments, samples should be shipped at room temperature.

In order to check for adherence appropriate protocols in a clinical setting, quality control methods, which are disclosed herein, may be employed. Quality control methods may be used to check for hemolysis, lipemia and sample storage conditions (e.g. whether the samples has remained at room temperature too long before serum extraction and storage). Particular quality control methods have been developed and are disclosed herein below. Included are methods for measuring hemolysis, lipemia, bilirubin contamination, contamination from certain storage vials, and time at room temperature before serum extraction.

Hemolysis and Lipemia Quality Control Measurements

Hemolysis (or hemolysis), from the Latin hemo (blood) and lysis (to break open), is the release of hemoglobin and other intracellular components from erythrocytes to the surrounding plasma, following damage or disruption of the cell membrane.

Lipemic plasma has large lipid particles that include lipoproteins and chylomicrons. As a result, these samples have increased sample turbidity and may result in the prolongation of coagulation results. Interference is variable among analyzers.

In certain embodiments, an increase in an optical absorbance measurement (e.g. measured via a NanoDrop® spectrophotometer) at wavelength of A414 is correlated with an increase in free hemoglobin concentration. In certain embodiments, measurements at a wavelength of A385 are indicative of lipemia. As used herein, the letter "A" preceding a number (e.g., as in "A385") refers to a wavelength of light where an absorbance peak is measured, wherein the number is the wavelength as expressed in nanometers (e.g., "measurements at A385" refers to measuring an absorbance peaks that occurs at a wavelength of 385 nm).

When both lipemia and hemolysis are present in the sample, measurements at A414 can be affected by presence of lipemia and thus cannot be taken as reliable measurements for evaluating hemolysis. Additionally, measurements at A660-700 may provide an alternative option to be used for characterizing lipemia (e.g. may be measured a with Roche Cobas® 6000 analyzer).

Since measurements of UV-Vis absorbance at individual wavelengths can be influenced by the presence of hemolysis and lipemia, metrics that can provide reliable indication of hemolysis, but are at the same time robust to variations in lipemia may be important. Similarly, a metric that is indicative of lipemia, but stable with regard to variations in hemolysis also may provide important indications of sample state.

An experiment was designed for artificially creating hemolysis and lipemia samples. Ultraviolet-visible (UV-Vis) absorbance measurements were carried out using a Nano-Drop® 2000c Spectrophotometer (Thermo Scientific, Barrington, Ill., USA) and were performed by applying 2 μL of sample on the micro-volume pedestal.

Linear regression models, R2 and coefficients of variation (CV) were computed using excel. Hemolysis correction factors and resulting HS scores were calculated using the NanoDrop results.

Sample collection was performed via the following protocol: (1) 1 volunteer-plasma sample in EDTA or heparin tube (2) Plasma and red blood cell (RBC) separation was performed straight away at 2000×g, 15 min, 4 degrees Celsius; (3) plasma should be stored at minus 80 degrees Celsius; (4) RBC should be vigorously mixed using a vortex and stored at 4 degrees Celsius until further use (5) for 3 volunteers, 20 mL of serum sample (3 vials) was collected under normal protocol (6.5 mL of serum per person minimum), (6) Samples were kept on ice during the whole hemolysis experiment process.

Following sample collection, a hemolysis assay was prepared and measured as follows:

(1) For each of the 3 volunteers, 500 μL of serum sample with 0.5% RBC content was prepared by mixing 497.5 μl serum with 2.5 μL of RBC. In particular, RBC1=0.5% hemolysis=497.5 μL PS+2.5 μL RBC.

(2) A serial dilution was prepared as follows (HS=hemolysis sample, PS=pure serum):

RBC2=0.25% hemolysis=100 μL of 0.5% HS+100 μL of PS

RBC3=0.125% hemolysis=100 μL of 0.25% HS+100 μL of PS

RBC4=0.0625% hemolysis=100 μL of 0.125% HS+100 μL of PS

RBC5=0.03125% hemolysis=100 μL of 0.0625% HS+100 μL of PS

RBC6=0.015625% hemolysis=100 μL of 0.03125% HS+100 μL of PS

RBC7=0.007813% hemolysis=100 μL of 0.015625% HS+100 μL of PS

RBC8=0.003906% hemolysis=100 μL of 0.007813% HS+100 μL of PS

RBC9=0.001953% hemolysis=100 μL of 0.003906% HS+100 μL of PS

The dilution series is shown in Table 3.

TABLE 3

Dilution series for a Hemolysis assay
Dilution Series

| 0.25 | 0.125 | 0.0625 | 0.03125 | 0.015625 | 0.007813 | 0.003906 | 0.001953 |
| --- | --- | --- | --- | --- | --- | --- | --- |

(3) Measurements with the Nanodrop at wavelengths of A414-385/A660-700 were recorded for each sample in the dilution series. The samples were then stored at −80° C. A measurement of a pure sample (RBC 0) was also taken.

A lipemia dilution series was prepared and measured similarly, according to the following steps:

(1) For each of the 3 volunteers, 2200 μL of serum sample with 0.8% lipid content was prepared according to L1=2182.4 μL PS+17.6 μL Lipofundin (lipofundin MCT 5 g+5 g/100 mL, B. Braun Melsungen Ag, Melsungen, Germany)=0.8% Lipemic sample (0.8% LP)

(2) A serial dilution from the 0.8% LP (Original LP) was then prepared as follows L2=0.4% lipemic sample(LP)=1015 μL of 0.8% LP+1015 μL of PS L3=0.2% lipemic sample(LP)=875 μL of 0.4% LP+875 μL of PS L4=0.1% lipemic sample(LP)=600 μL of 0.2% LP+600 μL of PS (3) Measurements with the Nanodrop at wavelengths of A414-385/A660-700 were recorded for each sample in the lipemia dilution series. The samples were then stored at −80° C.

Finally, a Hemolysis and Lipemia assay (RBC+LP) was prepared according to the following steps:

(1) For each of the 3 volunteers hemolysis+lipemic samples using different lipemia dilutions of each volunteer and making stepwise dilution for hemolysis as shown below in order to produce samples with varying levels of % hemolysis (according to the values shown in Table 4) in the presence of different levels of lipemia (0.8%, 0.4%, 0.2% and 0.1%):

TABLE 4

Dilution series for hemolysis for samples containing both hemolysis and lipemia.
Dilution Series

| 0.25 | 0.125 | 0.0625 | 0.03125 | 0.015625 | 0.007813 | 0.003906 | 0.001953 |
| --- | --- | --- | --- | --- | --- | --- | --- |

In detail:
Dilutions A:

RBC+L1A=199 μL of 0.8% LP+1 μL RBC=0.8% lipemia+0.5% HS

RBC+L2A=100 μL of RBC+L1A+100 μL of 0.8% LP=0.25% HS

RBC+L3A=100 μL of RBC+L2A+100 μL of 0.8% LP=0.125% HS

RBC+L4A=100 μL of RBC+L3A+100 μL of 0.8% LP=0.0625% HS

RBC+L5A=100 µL of RBC+L4A+100 µL of 0.8%
LP=0.03125% HS

RBC+L6A=100 µL of RBC+L5A+100 µL of 0.8%
LP=0.015625% HS

RBC+L7A=100 µL of RBC+L6A+100 µL of 0.8%
LP=0.007813% HS

RBC+L8A=100 µL of RBC+L7A+100 µL of 0.8%
LP=0.003906% HS

RBC+L9A=100 µL of RBC+L8A+100 µL of 0.8%
LP=0.001953% HS

Dilutions B:

RBC+L1B=199 µL of 0.4% LP+1 µL RBC=0.4%
lipemia+0.5% hemolysis.

Stepwise dilutions through 0.001953% were prepared as described above with regard to Dilutions A.

Dilutions C:

RBC+L1C=199 µL of 0.2% LP+1 µL RBC=0.2%
lipemia+0.5% hemolysis.

Stepwise dilutions through 0.001953% were prepared as described above with regard to Dilutions A.

Dilutions D:

RBC+L1D=199 µL of 0.1% LP+1 µL RBC=0.1%
lipemia+0.5% hemolysis.

Stepwise dilutions through 0.001953% were prepared as described above with regard to Dilutions A.

During the experiment it was found that not enough volume was left to have the dilutions of the last part of the experiment (RBC+L) and still keep enough volume of L dilutions to carry out MS analysis (at least 100 µL), so the last dilution amount of RBC+L was reduced following way:

RBCL9B,45 µL+45 µL=90 µL     Patient 1,

RBCL9C,50 µL+50 µL=100 µL     Patient 2,

RBCL9D,50 µL+50 µL=100 µL     Patient 2,

RBCL8A,70 µL+70 µL=140 µL     Patient 3,

RBCL9A,35 µL+35 µL=70 µL     Patient 3,

RBCL9B,50 µL+50 µL=100 µL     Patient 3,

RBCL9C,50 µL+50 µL=100 µL     Patient 3,

RBCL9D,50 µL+50 µL=100 µL     Patient 3, (2) As with the pure hemolysis and lipemia samples, measurements with the Nanodrop at wavelengths of A414-385/A660-700 were recorded for each sample in the hemolysis+lipemia dilution series. The samples were then stored at −80° C.

Measurements performed at the different wavelengths for the different dilutions are shown in Table 5, Table 6, and Table 7.

Graphics(L1 to L4): $y=\Delta 414-385$; $x=A385$; $a$=factor $HS=\Delta 414-385+(factor*A385)$ Table 5 shows Nanodrop measurements for samples with hemolysis, but no lipemia.

TABLE 5

Nanodrop measurements for directly evaluating hemolysis with A414-385 and by applying HS correction score.

| % hemolysis | % lipemia | | A385 | A414 | A414-385 | A660-700 | HS Score |
|---|---|---|---|---|---|---|---|
| 0 | 0 | RBC 10 | 0.066 | 0.120 | 0.054 | 0.004 | 0.068328 |
| 0.001953 | 0 | RBC 9 | 0.070 | 0.124 | 0.054 | 0.003 | 0.06912 |
| 0.003906 | 0 | RBC 8 | 0.071 | 0.130 | 0.059 | 0.001 | 0.074336 |
| 0.007813 | 0 | RBC 7 | 0.070 | 0.136 | 0.066 | 0.004 | 0.08112 |
| 0.015625 | 0 | RBC 6 | 0.074 | 0.154 | 0.080 | 0.002 | 0.095984 |
| 0.03125 | 0 | RBC 5 | 0.092 | 0.194 | 0.102 | 0.000 | 0.121872 |
| 0.0625 | 0 | RBC 4 | 0.098 | 0.245 | 0.147 | 0.003 | 0.168168 |
| 0.125 | 0 | RBC 3 | 0.141 | 0.400 | 0.259 | 0.002 | 0.289456 |
| 0.25 | 0 | RBC 2 | 0.212 | 0.666 | 0.454 | 0.004 | 0.499792 |
| 0.5 | 0 | RBC 1 | 0.388 | 1.277 | 0.889 | 0.005 | 0.972808 |

Figure 5:
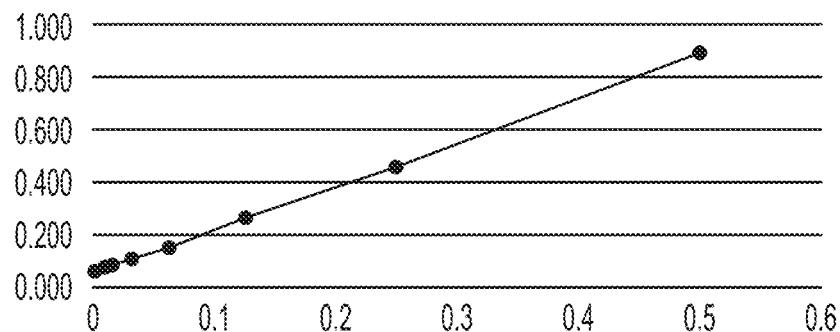
FIG. 5 shows a linear increase obtained with increase hemolysis for A414-385 values represented in Table 5, indicating good accuracy for using A414-385 as measurement on samples displaying only hemolysis.

FIG. 5 shows a linear increase obtained with increase hemolysis for A414-385 values represented in Table 5, indicating good accuracy for using Δ A414-385 as a measurement indicative of hemolysis for samples displaying only hemolysis.

Figure 6:
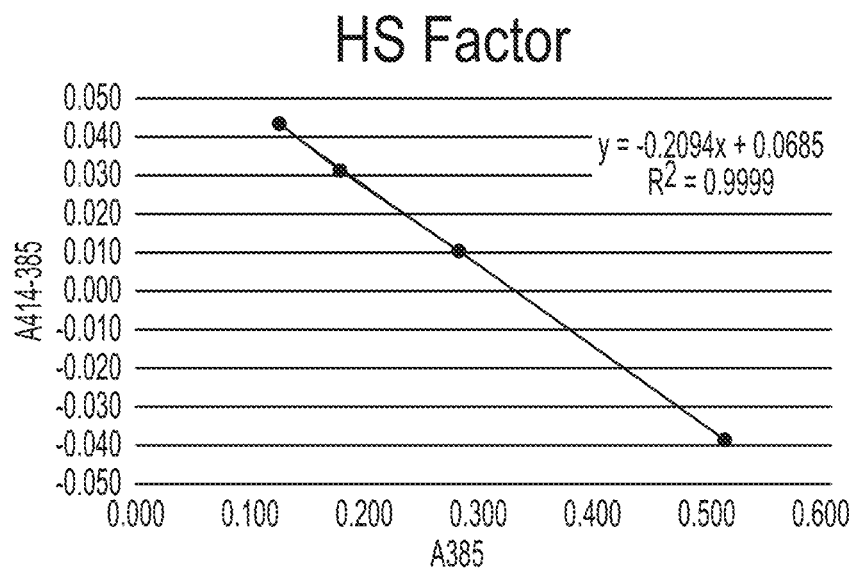
FIG. 6 shows a linear relationship between the extent of lipemia (in terms of A385 values, x axis) and A A414-A385 estimation (y axis) with a resulting quantitative relationship derived from a linear regression also shown.

A414-385 values were then measured for samples displaying both hemolysis and lipemia. All samples displayed a linear relationship between the extent of lipemia (in terms of A385 values) and Δ A414-A385 estimation (mean $R^2=0.996$, range $R^2=0.986$-$0.999$) following the trend line equation Δ A414−A385=a*A385+b (FIG. 6). The angular coefficient, a, was calculated for all samples and a mean absolute value of $|\bar{a}|=0.216$ (CV=2.9%) was obtained.

Samples with the same % hemolysis, but different % lipemia were found to have different A414-385 (Table 6) values. The HS score, however, was substantially the same across the samples. This indicates that for accurate evaluation on % hemolysis, HS Score should be used instead of simple A414-385 measurement.

TABLE 6

UV-Vis absorbance for samples with different lipemia levels and hemolysis levels. The lipemia levels influence the measurement of A414-385, while HS score appears robust to variations in lipemia

| % hemolysis | % lipemia | | A385 | A414 | A414-385 | A660-700 | HS Score |
|---|---|---|---|---|---|---|---|
| 0.001953 | 0.8 | RBC + L A 9 | 0.503 | 0.471 | −0.032 | 0.022 | 0.076648 |
| 0.001953 | 0.4 | RBC + L B 9 | 0.286 | 0.28 | −0.006 | 0.009 | 0.055776 |

TABLE 6-continued

UV-Vis absorbance for samples with different lipemia levels and hemolysis levels.
The lipemia levels influence the measurement of A414-385, while HS score appears robust to variations in lipemia

| % hemolysis | % lipemia | | A385 | A414 | A414-385 | A660-700 | HS Score |
|---|---|---|---|---|---|---|---|
| 0.001953 | 0.2 | RBC + L C 9 | 0.181 | 0.213 | 0.032 | 0.004 | 0.071096 |
| 0.001953 | 0.1 | RBC + L D 9 | 0.126 | 0.171 | 0.045 | 0.003 | 0.072216 |
| 0.003906 | 0.8 | RBC + L A 8 | 0.512 | 0.483 | −0.029 | 0.018 | 0.081592 |
| 0.003906 | 0.4 | RBC + L B 8 | 0.282 | 0.295 | 0.013 | 0.006 | 0.073912 |
| 0.003906 | 0.2 | RBC + L C 8 | 0.176 | 0.212 | 0.036 | 0.004 | 0.074016 |
| 0.003906 | 0.1 | RBC + L D 8 | 0.125 | 0.173 | 0.048 | 0.004 | 0.075 |

Measurements for evaluating lipemia in the presence of hemolysis were also evaluated. Table 7 shows measurements of A385 and A660-770 for a constant lipemia level and varying hemolysis. The A660-700 absorbance measurement does not vary substantially with % hemolysis. In contrast, the A385 measurement changes depending on the hemolysis level of the sample despite the % lipemia remaining constant. Accordingly, A660-700 may provide a more reliable measurement of lipemia in a sample, robust to variations in hemolysis, than the commonly used A385 measurement.

TABLE 7

Comparison of measurements of A385 and A660-700 for samples with varying % hemolysis and constant % lipemia

| % hemolysis | % lipemia | | A385 | A660-700 |
|---|---|---|---|---|
| 0.001953 | 0.8 | RBC + L A 9 | 0.503 | 0.022 |
| 0.003906 | 0.8 | RBC + L A 8 | 0.512 | 0.018 |
| 0.007813 | 0.8 | RBC + L A 7 | 0.51 | 0.022 |
| 0.015625 | 0.8 | RBC + L A 6 | 0.519 | 0.021 |
| 0.03125 | 0.8 | RBC + L A 5 | 0.534 | 0.020 |
| 0.0625 | 0.8 | RBC + L A 4 | 0.554 | 0.025 |
| 0.125 | 0.8 | RBC + L A 3 | 0.603 | 0.020 |
| 0.25 | 0.8 | RBC + L A 2 | 0.092 | 0.020 |
| 0.5 | 0.8 | RBC + L A 1 | 0.846 | 0.024 |

In certain embodiments, the methods described herein for determining the hemolysis and lipemia levels in a sample may be used as quality controls. For example, samples exhibiting higher levels of hemolysis and/or levels of lipemia may be excluded from analysis. In certain embodiments, measurements of lipemia and hemolysis may be applied as correction factors or additional parameters in the predictive model.

Time at Room Temperature Quality Control Marker

In certain embodiments, adequate serum extraction protocols are a key for successful measurement and estimation of the disease state of the patient. Accordingly, the influence of the time that blood samples were kept at room temperature prior to serum extraction on the markers was evaluated. Blood samples were extracted from 6 volunteers. For each volunteer 5 tubes of venous blood were collected and different extraction time-points were applied to each of the tubes ranging from 30 min, 2 h, 4 h, 8 h and 24 h from blood extraction. All samples were frozen after serum extraction and kept at −80 degrees Celsius for a couple of days. A metabolite extraction method was applied to all the samples according to a standard protocol. All samples were analyzed as 1 analysis set according to the analysis protocols based on, e.g. using FIA for fatty acid analysis, C18 columns for metabolite analysis, and Amide columns for polar metabolite analysis.

Certain markers measured via the Amide and C18 columns were affected by serum time at room temperature from 2 hours forward. The majority of affected markers had a considerable increase after 4 hours at room temperature which correlates with our strict sample collection protocol for prospective sample collection.

The marker S150 was found to be strongly influenced by time at room temperature. The marker measurement showed an increase of 23% on average for extraction times of 2 h in comparison with extraction times of 30 min. An exponential increase was observed as a function of time to extraction for times up to 24 h.

In one embodiment, based on measurements of S150 and mass spectrometric measurements on over 1000 individual stored samples an estimated value of 15 μg/mL was determined as a cut-off for exclusion of the sample from further analysis. S150 values higher than 15 μg/mL correlated with concentration measurements for other markers that were either increased or decreased from their normal values and would therefore lead to inaccurate sample classification.

Sample Collection Quality Control Marker

In one embodiment, a comparison of different sample sources and collection methods indicated that S10 is a marker indicating a certain type of collection protocol used. In certain embodiments, under normal collection protocols the values of S10 are 10 times lower than under inappropriate sample collection protocol using collection tubes. As appropriate collection is prerequisite for accurate metabolic measurements, this marker may be used as an indicator for sample collection that can result in inaccurate classification. Accordingly, in certain embodiments, measurement of the S10 marker may be used as a quality control measure.

Markers for Icterus Measurements

Icterus may cause an excess of bilirubin pigment or bilirubin complexes in the bloodstream. The bilirubin pigment or bilirubin complexes may interfere with spectrophotometric measurements.

Three molecules from bile acid pathway (S52, S61 and S62) can be measured with the systems and methods described herein. These molecules are believed to connected to jaundice and liver dysfunction, which can result in bilirubin accumulation.

Internal Standards for Mass Spectrometry Measurements

In certain embodiments, methods and protocols that improve the accuracy and reproducibility of the mass spectrometry measurement itself are also important to employ.

For example, before measuring an experimental sample, it is necessary to stabilize the mass spectrometry equipment by running 5-10 quality control samples. Mass spectrometry equipment is prone to giving false results before stabilization and, accordingly, the first 5-10 quality control sample measurements should be discarded. Additional quality control and blank samples need to be run during after every 10 analysis samples. Moreover, additional quality control can be provided by running all analysis samples in duplicate. For example, samples that have a CV %>20 between duplicate samples for more than 20% of the markers are excluded from the further analysis. The sample preparation procedure is repeated for these samples.

In certain embodiments, isotopically labelled internal standards are useful to include in order to enable accurate and reproducible quantification of a molecule of interest (e.g. a marker). For example, S192 (3Me-Glutaryl Carnitine) is an important marker in panels, but was challenging to measure without a proper internal standard.

An isotopically labelled internal standard may be a synthetic equivalent of the molecule of interest that is modified by replacing specific atoms by their isotopes. A known concentration of the standard is then artificially added to the sample to be analyzed (e.g. a serum sample) and extracted and analyzed alongside the biological molecule of interest. As the concentration of the synthetic molecule is known then the concentration of the biological molecule can be calculated with the help of fitting the synthetic one to a calibration curve of the method.

There were 11 metabolites (listed in Table 8) that do not have commercially available internal standards. Custom standards were synthesized for these molecules.

TABLE 8

List of molecules that required custom synthesis a corresponding internal standard.

| | IS |
|---|---|
| Marker AMIDE | |
| S325 | CUSTOM SYNTHESIS |
| S179 | CUSTOM SYNTHESIS |
| Marker C18 | |
| S103 | CUSTOM SYNTHESIS |
| S168 | CUSTOM SYNTHESIS |
| S295 | CUSTOM SYNTHESIS |
| S166 | CUSTOM SYNTHESIS |
| S175 | CUSTOM SYNTHESIS |
| S227 | CUSTOM SYNTHESIS |
| S285 | CUSTOM SYNTHESIS |
| S3 | CUSTOM SYNTHESIS |
| S192 | CUSTOM SYNTHESIS |

Biomarker Discovery Approach

An example biomarker discovery approach, which was used to discover the list of markers provided herein is also included in the following.

In the embodiment, five different approaches (untargeted profiling of metabolites, targeted detection of lipids (e.g., fatty acids), utilization of Biocrates targeted analysis kit, utilization of targeted metabolite panel offered by Metabolon Inc. and literature and database search over metabolites that have been connected to cancer and its progression) and 4 different analytical platforms (LC-MS on Agilent QTOF with C18 50 mm column and Amide column, LC-MS on AB Sciex QTRAP with C18 100 mm column and FIA (flow injected analysis) injection on ABSciex QTRAP) were used to identify significant markers.

A first step in the example assay development process as described herein was biomarker discovery using 5 different approaches (e.g., untargeted profiling with LC-MS on Agilent QTOF, e.g., utilization of Biocrates targeted analysis kit on ABSciex 5500 QTRAP, e.g., outsourcing of lipid analysis from Lipotype GmbH, e.g. FIA injection on ABSciex TQ 4500MD, e.g. targeted profiling by Metabolon Inc.) to pool out significant markers. A total of 505 samples were analyzed of which 450 belonged to CRC analysis panel and 55 were lung cancer samples were analyzed across those 5 approaches.

A serum-based global metabolic profiling test was performed to detect biomarkers that are indicative of certain health state. The initial biomarker discovery study was based on using untargeted profiling technique utilizing liquid chromatography coupled mass spectrometry equipment for screening total of 415 samples. This type of screening option allows detection of and provides intensity values for hundreds of different small molecules present in human sera. Together with appropriate statistical tools, a set of significant markers were identified.

The biomarker discovery process also used additionally a targeted approach by analyzing 202 samples. In certain embodiments, AbsoluteIDQ p180 Kit was used, produced and provided by Biocrates Life Sciences AG. AbsoluteIDQ p180 Kit can be used for targeted detection and quantification of 186 pre-defined molecules belonging to different metabolite and lipid classes. A sample set used for this part of the biomarker discovery partially overlapped with global profiling experiments that were performed previously and partially employed new samples.

Lipid analysis was outsourced from Lipotype GmbH, Dresden, Germany. The samples were provided to Lipotype GmbH, who performed the sample preparation and analysis. Lipotype GmbH provided a list of lipids with semi-quantitative values as result. A sample set of 120 samples was used in this targeted profiling method. This sample set overlapped with the samples used in the untargeted profiling approach.

A search into published literature and biological pathways was also performed to find markers that might be influenced by cancer development. The most significant finding from this search was 6 polyunsaturated fatty acids—PUFA molecules. Structurally, the molecules resemble very long chain (28 carbon) mimetics of the resolvins and protectins, containing multiple double bonds and at least two hydroxyl groups. FIG. 1 shows a structure of the 6 molecules.

In addition to all the previous discovery phase another outsourcing option was used by performing targeted profiling experiment on 120 samples and 800 identified putative identification markers designed into 1 panel by Metabolon Inc. This sample set overlapped with the samples used in untargeted profiling approach.

Significant markers were identified from the 5 different discovery approaches and combined using feature selection and statistical pattern recognition methods as described herein.

A second step in the example process was optimization of analytical platforms for the significant markers identified. A first analytical panel of 18 markers generated was tested with new set of 369 samples for verifying the performance. After combining significant markers from all these 5 discovery options another set of optimization and significant feature selection experiments were performed to verify and fix the panel to the list shown in FIG. 1. After additional identification, method optimization and a second phase of feature selection a panel of 78 markers for LC-MS based analysis that has been divided into 3 methods according to separation column (as specified above) was obtained. An additional 6 markers to be measured with FIA-MS analysis was also found. Overall, 84 markers to be measured using distinct analysis methods were found (FIG. 1 and Table 1). Results based on 678 new samples and 30 metabolic markers are presented in further paragraphs on this document.

Additional Panel Study Using 30 Metabolic Markers

In an example study, the performance of a 30 metabolic marker panels based on a subset of the markers listed in Table 1 and Table 2 was further evaluated using 682 retrospective samples from a population of patients from Spain, Ukraine, Russia, UK and USA. Samples were obtained from following sources (Hospital Victoria Eugenia, Sevilla, Spain, IDIBAPS biobank Barcelona Spain, Asterandbio biobank USA (with collection from Russia and Ukraine, Biosevere USA, Biooption USA, Folio USA, Promeddex USA and Tissuesolution Glasgow UK). Patients with all stages of colorectal cancer, individuals without diseases of the colon as verified by colonoscopy, additional disease controls, and a number of patients with adenomatous polyps were included.

General sample collection rules were as follows. Blood from adenoma, a subset of CRC patients, and control subjects had been drawn prior colonoscopy. Blood was drawn for a subset of CRC patients prior to starting any cancer specific treatment. Cancer diagnosis was confirmed histologically from the surgical specimen. A subset of the controls used was not verified to be adenoma free by colonoscopy, but they were believed to be cancer free. All subjects participating had neither a personal history of HIV, HBV or HCV, nor previous history of cancer. Serum was extracted and frozen down within 4 hours from drawing blood from the patients. Samples were collected under fasting conditions and stored at −80° C.

Serum samples were stored at −80° C. until thawed for analysis. Samples were only thawed once. Samples were kept on ice until extraction process that was performed at room temperature. Serum samples were prepared for MS analysis by first sequentially extracting serum with a 3:1 volume of ice cold methanol. Samples were incubated and centrifuged at 4° C. for 10 min at 3500 rpm and the organic layer was removed and transferred to a new tube (extract A). Extract A was then completely evaporated under nitrogen and reconstituted in original sample volume of ACN:H2O 5:95 (extract B). All extracts were either stored at −80° C. or analyzed straight away with MS.

A panel of 30 different markers was measured with 3 different methods-FIA based direct infusion injection for analyzing fatty acid markers, LC-MS C18 50 mm column based method for metabolite detection and LC-MS Amide column based metabolite detection method. In particular, 30 MRM transitions were analyzed with the 3 different MS methods. Fifteen markers were measured using conventional reverse phase chromatography, 9 polar compounds were measured in an amide column method and 6 markers were measured via direct injection method with FIA. A list of the metabolites along with the corresponding measurement method is shown in Table 9. These markers are a subset of the markers listed in the table shown in Table 1. These metabolites belong to 6 different major chemical classes (such as amino acids and their derivate, vitamin derivate, carboxylic acids, dipeptides, micronutrients, nucleosides, carnitines, lipids and fatty acids), which are located in important metabolic pathways (e.g., TCA cycle, amino acid metabolism, glycolysis, lipid metabolism, Krebs cycle), in both positive and negative ionization modes.

TABLE 9

| List of markers | |
| --- | --- |
| S1 | C18 |
| S63 | C18 |
| S100 | C18 |
| S103 | C18 |
| S109 | C18 |
| S147 | C18 |
| S193 | C18 |
| S227 | C18 |
| S69 | C18 |
| S166 | C18 |
| S3 | C18 |
| S192 | C18 |
| S76 | C18 |
| S175 | C18 |
| S285 | C18 |
| S10 | C18 |
| S150 | C18 |
| S168 | C18 |
| S295 | C18 |
| S125 | Amide |
| S132 | Amide |
| S153 | Amide |
| S236 | Amide |
| S261 | Amide |
| S49 | Amide |
| S110 | Amide |
| S78 | Amide |
| S111 | Amide |
| S179 | Amide |
| S325 | Amide |
| PUFA 446 | FIA |
| PUFA 448 | FIA |
| PUFA 450 | FIA |
| PUFA 464 | FIA |
| PUFA 466 | FIA |
| PUFA 468 | FIA |

Two calibration curves were prepared to quantify all markers of the panel. Curve 1 contains 6 calibration levels and curve 2 contains 8 calibration levels. Calibrators were prepared freshly every day.

SeraSub® was used as a blank matrix. SeraSub is a synthetic polymer in buffered solution that is physically equivalent to serum and plasma with respect to specific gravity, viscosity and osmolality.

Standard 6 (STD 6) and standard 8 (STD 8) from curves 1 and 2 respectively, were used to build the other standards by serial dilutions.

In the present example study, all samples, quality control samples and blank standards were prepared as one analysis set and analyzed in one analysis run. Blank samples and QC samples were analyzed every 10 samples for evaluating stability of the system over a long run and applying normalization for the samples. All samples were analyzed in duplicates. A CV<20% QCs run between all analysis sets performed in different days was considered acceptable. Raw data was transformed into area values using the MultiQuant software tool from ABSciex. MultiQuant software is used for evaluating the integrity of the peaks generated via analysis, and for integrating peak values in order to obtain absolute concentration. Stable isotope-labeled internal standards were used for 15 markers measured via reverse phase chromatography, and 9 markers measured via amide column for absolute quantification purposes, and for monitoring instrument performance.

In the embodiment, data analysis was performed using a random forest classifier, based on the remaining 30 markers. In addition to the measured concentration of the markers, additional features were generated by taking the ratios of the measurements between individual markers. The resulting 400+ratios were evaluated for their performance and correlation, and the best combinations were used for training the model. A subset of 317 samples was used to generate the training set algorithm, and 365 samples were used in the testing study. A balanced training dataset independent from physical factors such as age, race or gender was built. The three conditions that were met in the training dataset have balanced distributions regarding age, gender and race. The demographic and clinical parameters of the subjects included in the training study are outlined in Table 10.

TABLE 10

Clinical data of the sample set used for training the algorithm

|  |  | CRC | | | | | Polyp | | |
| --- | --- | --- | --- | --- | --- | --- | --- | --- | --- |
|  |  | Stage I | Stage II | Stage III | Stage IV | Unknown | AA | Non AA | Unknown |
| Age | <60 | 16 | 14 | 18 | 8 | 1 | 33 | 21 | 8 |
|  | 60-70 | 10 | 16 | 20 | 9 | 3 | 36 | 19 | 8 |
|  | 70-80 | 5 | 4 | 6 | 6 | 5 | 8 | 15 | 1 |
|  | >=80 | 0 | 1 | 4 | 0 | 1 | 0 | 1 | 1 |
| Gender | Female | 14 | 20 | 17 | 14 | 6 | 36 | 28 | 9 |
|  | Male | 17 | 15 | 31 | 9 | 4 | 41 | 28 | 9 |
| Race | Black | 0 | 0 | 0 | 0 | 0 | 0 | 1 | 0 |
|  | Caucasian | 31 | 34 | 48 | 23 | 10 | 76 | 55 | 18 |
|  | Hispanic | 0 | 1 | 0 | 0 | 0 | 0 | 0 | 0 |
|  | Other | 0 | 0 | 0 | 0 | 0 | 1 | 0 | 0 |

Monte-Carlo cross-validation was performed over the full sample set according following parameters:
Random Forest Classifier
  Ntree=1000
  Mtry=sqrt(#Markers)
  Monte Carlo Cross Validation (20 fold)
To confirm the performance of training algorithm an independent patient set was used. The testing set was comparable to training set with regard to age, gender and stage distribution for CRC and polyps. The distribution of the testing set is shown in Table 11.

TABLE 11

Clinical data of the sample set used for testing the algorithm

|  |  | CRC | | | | | | |
| --- | --- | --- | --- | --- | --- | --- | --- | --- |
|  |  | Stage I | Stage II | Stage III | Stage IV | Unknown | Polyp | Control |
| Age | <60 | 14 | 10 | 11 | 7 | 2 | 55 | 55 |
|  | 60-70 | 7 | 12 | 15 | 6 | 2 | 49 | 51 |
|  | 70-80 | 4 | 6 | 3 | 5 | 3 | 18 | 17 |
|  | >=80 | 1 | 0 | 3 | 0 | 2 | 2 | 4 |
| Gender | Female | 11 | 15 | 12 | 13 | 3 | 58 | 59 |
|  | Male | 15 | 13 | 20 | 5 | 6 | 66 | 69 |
| Race | Other | 0 | 1 | 0 | 0 | 0 | 4 | 0 |
|  | Caucasian | 26 | 27 | 32 | 18 | 9 | 120 | 128 |
| SUM |  |  |  |  |  | 113 | 124 | 128 |

Figure 7:
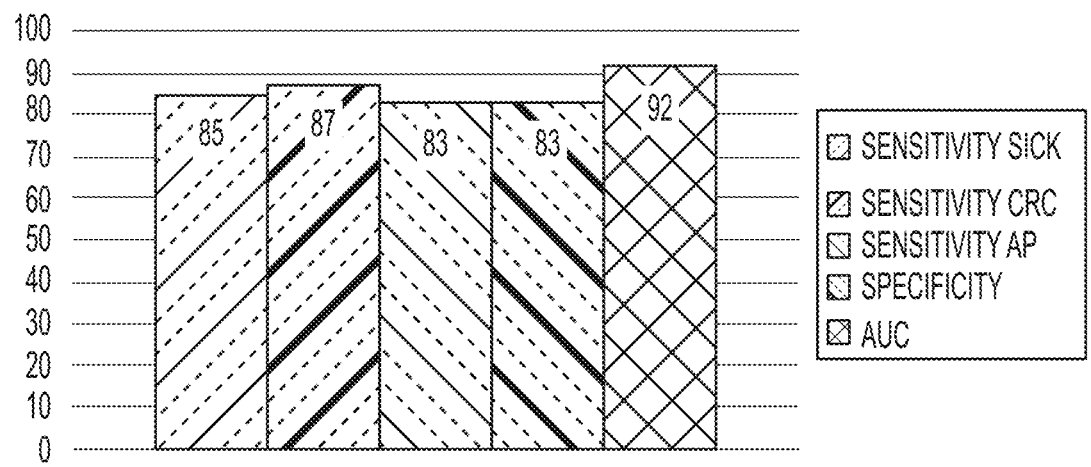
FIG. 7 shows the sensitivity and specificity of a marker panel based on the list of markers in Table 9.
Figure 8:
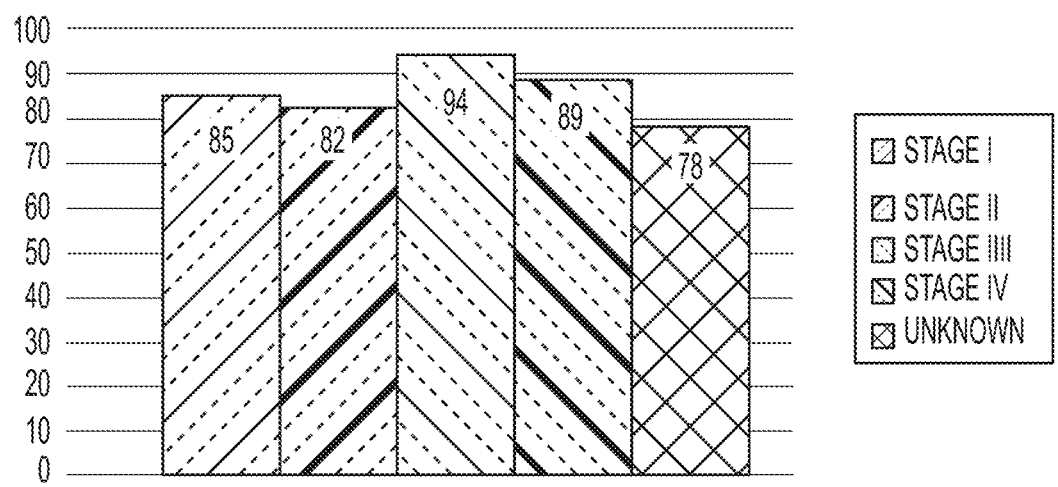
FIG. 8 shows the sensitivity of a marker panel in detecting the different stages of CRC based on the list of markers in Table 9.

Using the model threshold determined in the training study, the panel performance was confirmed in the testing set of 365 CRC, polyp and control patients. An AUC of 92% and a CI in the range (88.45%, 95.8%) were determined. Sensitivity and specificities of 87% and 83% were also determined, as shown in FIG. 7. There was no significant difference in detection rate by age or gender. Sensitivity for detecting only colorectal cancer regardless of the stage was 87 and sensitivity of detecting cancer of different stages ranged from 82-85% in early stage to 89-94% in later stages, as shown in FIG. 8. Adenomatous polyps were detected with general sensitivity of 83% (FIG. 7).

Certain features—corresponding to either ratios of two markers or particular markers measured in isolation—were found to be significant in distinguishing between patients with CRC and the control group, or between PP and the control group, when used in isolation.

The features relevant for CRC detection are listed in Table 12. The features relevant for detecting adenomatous polyps are listed in Table 13. The features based on a ratio of two markers as opposed to a measurement of a single marker appear to perform particularly well. It is important to note that these values represent univariate performance, meaning they are values representing the single feature performance (single marker in this sense means also a ratio), not the final panel. Markers in the panel that are not highly indicative as individual markers still contribute to the performance of the classification model that uses the overall panel. Certain molecules referred to in Table 12 and Table 13 are represented in FIG. 1 and FIG. 2.

Figure 9:
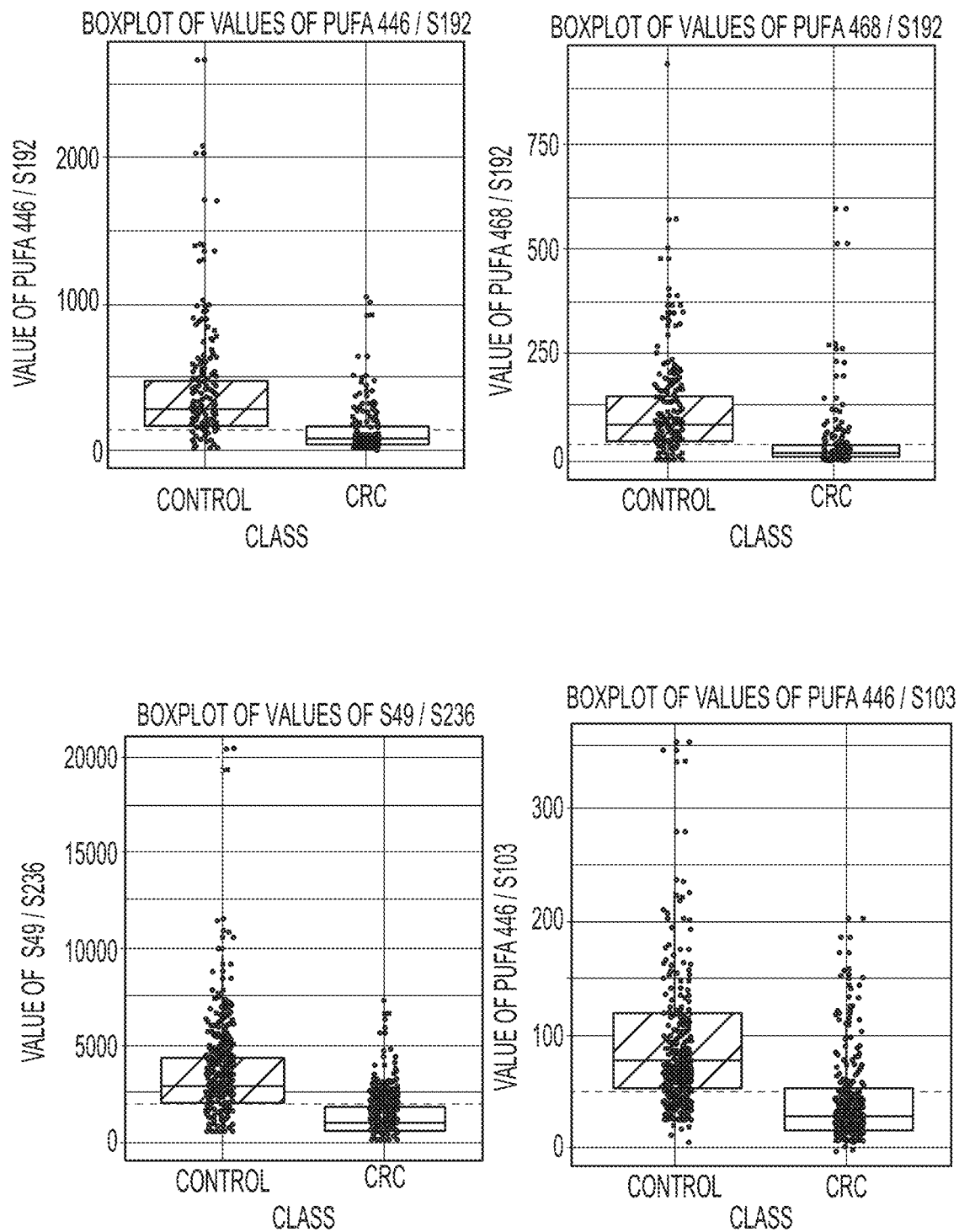
FIG. 9 shows an example of 4 individual features (markers or ratios of two markers) that have high significance for detecting colorectal cancer (the markers are selected from the subset listed in Table 9)
Figure 10:
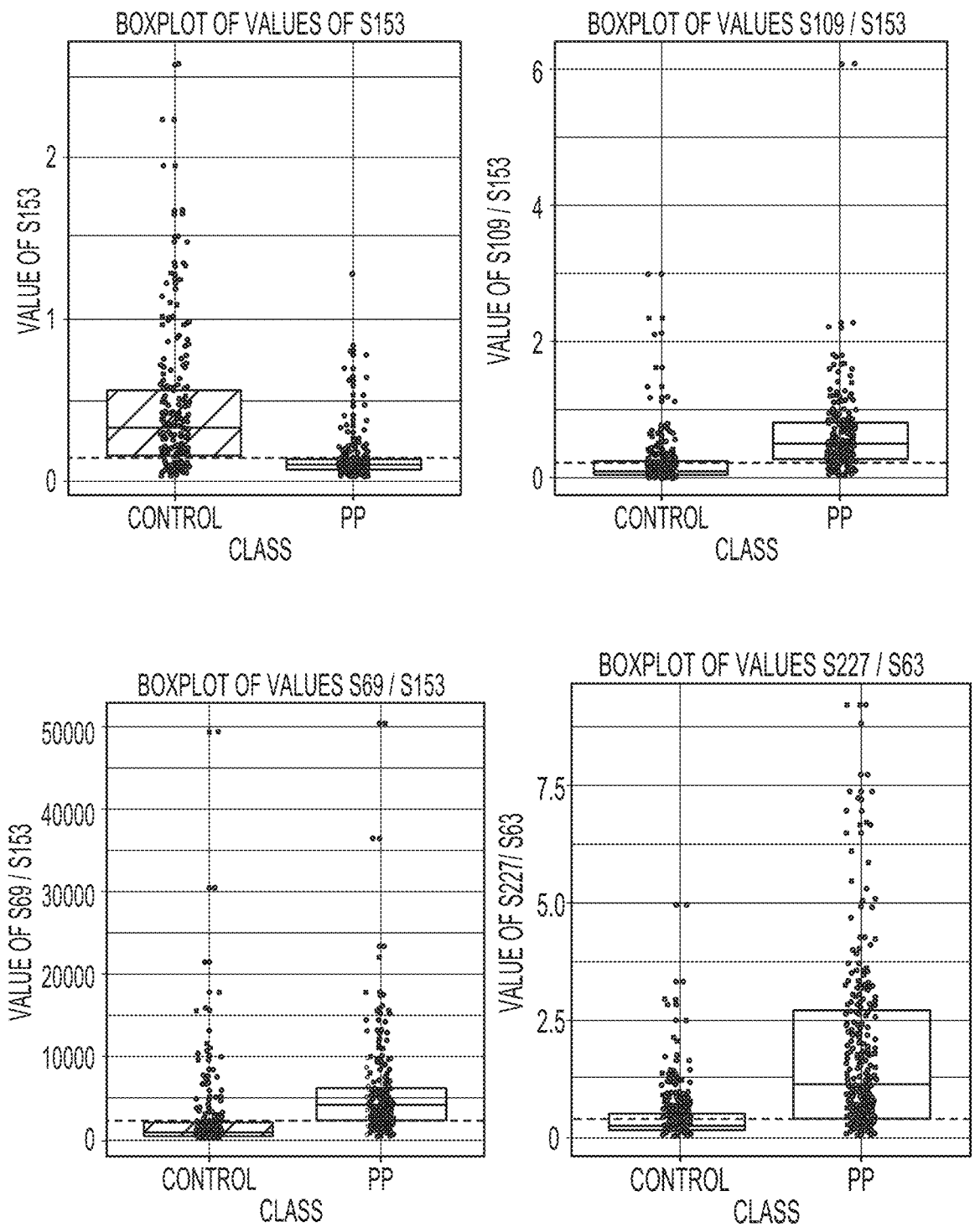
FIG. 10 shows an example of 4 individual features (markers or ratios of two markers) that have high significance for detecting adenomatous polyps (the markers are selected from the subset listed in Table 9).

FIG. 9 shows box plots of markers or ratios of markers in Table 12 that have high significance for detecting colorectal cancer. Experimental values for each marker or ratio of markers are shown for a population with colorectal cancer and a control population. The selectivity is qualitatively observed as the difference in distributions between the control population and the population having colorectal cancer. Calculated measures of selectivity are listed in Table 12. FIG. 10 shows box plots of markers or ratios of markers in Table 13 that have high significance for detecting adenomatous polyps as compared to a control. Experimental values for each marker or ratio of markers are shown for a population with adenomatous polyps and a control population. The selectivity is qualitatively observed as the difference in distributions between the control population and the population having adenomatous polyps. Calculated measures of selectivity are listed in Table 13.

TABLE 12

Significant markers for distinguishing between CRC vs Control ranked based upon their univariate performance

| Name | Kappa | Sensitivity | Specificity | AUC | Accuracy |
| --- | --- | --- | --- | --- | --- |
| PUFA 446/S192 | 0.55 | 0.72 | 0.83 | 0.83 | 0.77 |
| PUFA 468/S192 | 0.54 | 0.74 | 0.80 | 0.82 | 0.77 |
| S49/S236 | 0.52 | 0.76 | 0.76 | 0.83 | 0.76 |
| PUFA 446/S103 | 0.51 | 0.73 | 0.77 | 0.81 | 0.75 |
| PUFA 468/S285 | 0.50 | 0.77 | 0.73 | 0.81 | 0.75 |
| PUFA 446 | 0.50 | 0.68 | 0.82 | 0.79 | 0.75 |
| PUFA 468/S76 | 0.49 | 0.67 | 0.83 | 0.79 | 0.75 |

TABLE 12-continued

Significant markers for distinguishing between CRC vs Control ranked based upon their univariate performance

| Name | Kappa | Sensitivity | Specificity | AUC | Accuracy |
| --- | --- | --- | --- | --- | --- |
| PUFA 468 | 0.47 | 0.68 | 0.78 | 0.77 | 0.73 |
| S3/S236 | 0.46 | 0.70 | 0.76 | 0.80 | 0.73 |
| PUFA 468/S103 | 0.46 | 0.69 | 0.76 | 0.80 | 0.73 |
| PUFA 448 | 0.46 | 0.64 | 0.81 | 0.78 | 0.73 |
| S175/S236 | 0.45 | 0.70 | 0.75 | 0.80 | 0.72 |
| S1/S236 | 0.45 | 0.68 | 0.76 | 0.78 | 0.72 |
| PUFA 450/S103 | 0.45 | 0.67 | 0.78 | 0.80 | 0.72 |
| S132/S236 | 0.44 | 0.68 | 0.77 | 0.77 | 0.72 |

TABLE 13

Significant markers for distinguishing between PP vs Control ranked based upon their univariate performance

| Name | Kappa | Sensitivity | Specificity | AUC | Accuracy |
| --- | --- | --- | --- | --- | --- |
| S153 | 0.56 | 0.77 | 0.78 | 0.80 | 0.78 |
| S69/S153 | 0.55 | 0.80 | 0.75 | 0.82 | 0.78 |
| S109/S153 | 0.55 | 0.72 | 0.83 | 0.83 | 0.78 |
| S227/S63 | 0.45 | 0.76 | 0.69 | 0.78 | 0.72 |
| S109/S63 | 0.44 | 0.64 | 0.81 | 0.75 | 0.72 |

What is claimed is:

1. A method comprising:
   (a) measuring, by mass spectrometry, a level of each of a plurality of species in a biological sample obtained from a body fluid of a human subject, wherein each of the plurality of species is at least one of a metabolite and a fatty acid and the plurality of species comprises:

(PUFA 446)

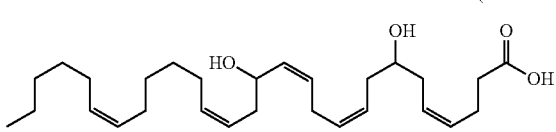

and 3Me-glutaryl carnitine (S192: 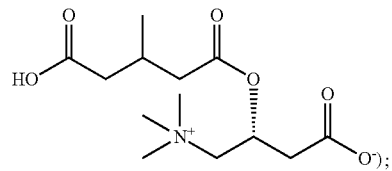);

(b) determining a ratio of the measured level of PUFA 446 and the measured level of S192; and
   (c) determining at least one of, a presence of, a stage of, and a risk of colorectal cancer in the human subject based, at least in part, on the ratio of the measured level of PUFA 446 and the measured level of S192.

2. The method of claim 1, wherein the plurality of species comprises one or more members in addition to PUFA 446 and S192 selected from the group consisting of the species listed in Table 12 and Table 13.

3. The method of claim 1, further comprising one or both of (i) and (ii):
   (i) determining at least one of a presence of, a stage of, and a risk of colorectal cancer in the human subject further based, at least in part, on measured values for one or more markers or marker ratios listed in Table 12; and/or
   (ii) determining at least one of a presence of, a stage of, and a risk of adenomatous polyps in the human subject based, at least in part, on measured values for one or more markers or marker ratios listed in Table 13.

4. The method of claim 1, wherein the measuring step comprises measuring the level of each of the plurality of species using a LC-MS, GC-MS, DESI, or DART technique.

5. The method of claim 1, wherein step (c) comprises:
   determining at least one of a presence of, a risk of, and a stage of colorectal cancer based, at least in part, on a ratio of the measured level of a polyunsaturated fatty acid of the plurality of species and the measured level of another of the plurality of species being lower than a representative ratio for a control population.

6. The method of claim 5, wherein the polyunsaturated fatty acid is a species listed in FIG. 1.

7. The method of claim 1, comprising:
   determining at least one of a presence of, a risk of, and a stage of colorectal cancer further based, at least in part, on a ratio of the measured level of choline (S49) and the measured level of N1, N12-diacetylspermine (S236) being lower than a representative ratio for a control population.

8. The method of claim 1, wherein at least one of the plurality of species is selected from the group consisting of:

(PUFA 468)

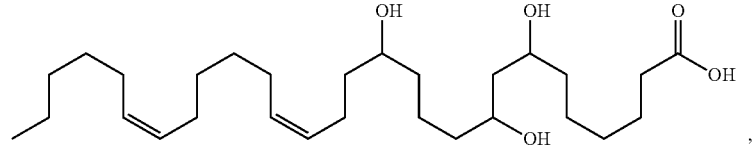

, (PUFA 464)

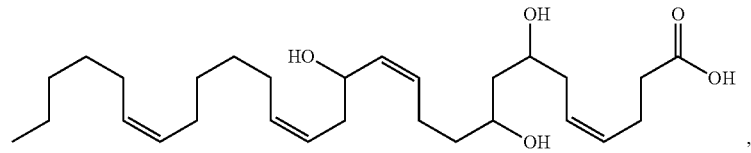

,

-continued

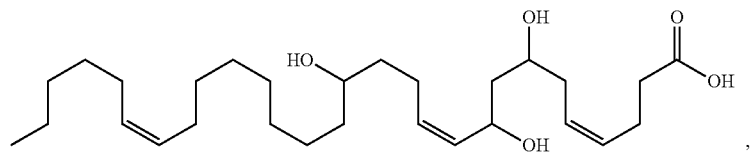
(PUFA 466)

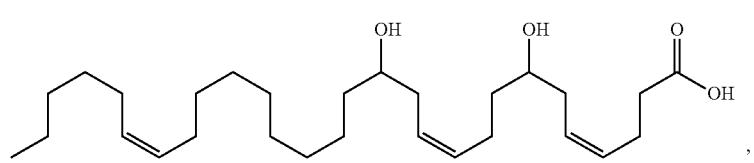
, and (PUFA 450)

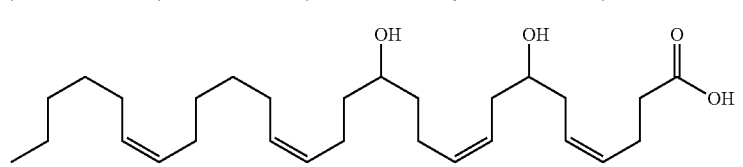
(PUFA 448)

9. The method of claim 1, wherein the biological sample comprises serum.

10. The method of claim 1, wherein the biological sample is serum, plasma, urine, saliva, whole blood, a dried blood spot, or a dried serum spot.

11. The method of claim 1, comprising:
introducing at least a portion of the biological sample into a C18 50 mm column, a C18 100 mm column, or an amide column to determine a quantification of metabolites, lipids or polar metabolic compounds, respectively, of the plurality of species.

12. The method of claim 1, comprising:
introducing at least a portion of the biological sample into a mass spectrometer by FIA based direct infusion injection to measure the level of a polyunsaturated fatty acid of the plurality of species.

13. The method of claim 1, comprising measuring a stable isotopically labeled reference standard.

* * * * *